(12) United States Patent
Keaney et al.

(10) Patent No.: US 10,745,387 B2
(45) Date of Patent: Aug. 18, 2020

(54) CRYSTALLINE FORM OF (2S,3S,6S,7R,10R, E)-7,10-DIHYDROXY-3,7-DIMETHYL-12-OX-O-2-((R,2E,4E)-6-(PIRIDIN-2-YL)HEPTA-2,4-DIEN-2-YL)OXACYCLODODEC-4-EN-6-YL-4-METHYLPIPERAZINE-1-CARBOXYLATE AND METHODS OF USE THEREOF

(71) Applicant: EISAI R&D MANAGEMENT CO., LTD., Tokyo (JP)

(72) Inventors: Gregg F. Keaney, Lexington, MA (US); John Wang, Andover, MA (US); Baudouin Gerard, Belmont, MA (US); Kenzo Arai, Tsukuba (JP); Xiang Liu, Winchester, MA (US); Guo Zhu Zheng, Lexington, MA (US); Kazunobu Kira, Tsukuba (JP); Parcharee Tivitmahaisoon, Boston, MA (US); Sudeep Prajapati, Somerville, MA (US); Nicholas C. Gearhart, Durango, CO (US); Yoshihiko Kotake, Tsukuba (JP); Satoshi Nagao, Tsukuba (JP); Regina Mikie Kanada Sonobe, Tsukuba (JP); Masayuki Miyano, Tsukuba (JP); Norio Murai, Tsukuba (JP); Silvia Buonamici, Boston, MA (US); Lihua Yu, Acton, MA (US); Eunice Sun Park, Arlington, MA (US); Betty Chan, Harvard, MA (US); Peter G. Smith, Arlington, MA (US); Michael P. Thomas, Stoneham, MA (US); Ermira Pazolli, Wayland, MA (US); Kian Huat Lim, Burlington, MA (US); Atsushi Endo, Andover, MA (US); Arani Chanda, Malden, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 177 days.

(21) Appl. No.: 15/529,798

(22) PCT Filed: Nov. 17, 2016

(86) PCT No.: PCT/US2016/062525
§ 371 (c)(1),
(2) Date: May 25, 2017

(87) PCT Pub. No.: WO2017/087667
PCT Pub. Date: May 26, 2017

(65) Prior Publication Data
US 2019/0100513 A1    Apr. 4, 2019

Related U.S. Application Data

(60) Provisional application No. 62/257,088, filed on Nov. 18, 2015.

(51) Int. Cl.
*A61K 31/496* (2006.01)
*C07D 295/182* (2006.01)
(Continued)

(52) U.S. Cl.
CPC ............ *C07D 405/14* (2013.01); *A61P 35/02* (2018.01); *C07D 405/06* (2013.01); *C07B 2200/13* (2013.01)

(58) Field of Classification Search
CPC .......................... A61K 31/496; C07D 295/182
(Continued)

(56) References Cited

U.S. PATENT DOCUMENTS 7,026,352 B1   4/2006  Mizui et al.
9,481,669 B2 * 11/2016  Keaney ............... C07D 405/06
(Continued)

FOREIGN PATENT DOCUMENTS

EP    1 380 579 A1    1/2004
EP    2 136 209 A1   12/2009
(Continued)

OTHER PUBLICATIONS

PCT Notification of Transmittal of the International Search Report and the Written Opinion of the International Searching Authority, issued in International Application No. PCT/US2016/062525, and dated Feb. 10, 2017, 12 pages.
(Continued)

*Primary Examiner* — Douglas M Willis
(74) *Attorney, Agent, or Firm* — Finnegan, Henderson, Farabow, Garrett & Dunner, LLP

(57) ABSTRACT

The present disclosure provides a novel solid state form of pladienolide pyridine compounds having Formula I, compositions comprising at least one such solid state form, and methods of preparation and use and the same. The novel solid state form of pladienolide pyridine compounds may be useful in the treatment of cancer, such as, for example, cancers in which agents that target the spliceosome and mutations therein are known to be useful.

26 Claims, 7 Drawing Sheets

(51) Int. Cl.
    *C07D 405/14* (2006.01)
    *C07D 405/06* (2006.01)
    *A61P 35/02* (2006.01)
(58) Field of Classification Search
    USPC ...................................... 514/252.1; 544/406
    See application file for complete search history.

(56) References Cited

U.S. PATENT DOCUMENTS

| | | | |
|---|---|---|---|
| 2005/0245514 | A1 | 11/2005 | Kotake et al. |
| 2006/0009439 | A1 | 1/2006 | Kotake et al. |
| 2006/0079572 | A1 | 4/2006 | Mizui et al. |
| 2006/0141589 | A1 | 6/2006 | Okuda et al. |
| 2006/0235002 | A1 | 10/2006 | Nagai et al. |
| 2007/0199741 | A1 | 8/2007 | Noumi |
| 2008/0070286 | A1 | 3/2008 | Machida et al. |
| 2008/0112956 | A1 | 5/2008 | Nakamura et al. |
| 2008/0312317 | A1 | 12/2008 | Miyano et al. |
| 2009/0215134 | A1 | 8/2009 | Machida et al. |

FOREIGN PATENT DOCUMENTS

| | | |
|---|---|---|
| EP | 2 145 886 A1 | 1/2010 |
| RU | 2394906 C2 | 7/2010 |
| RU | 2707730 C2 | 11/2019 |
| WO | WO 2008/126918 A1 | 10/2008 |
| WO | WO 2015/175594 A1 | 11/2015 |

OTHER PUBLICATIONS

Bernstein, J. "Polymorphism in Molecular Crystals." Oxford University Press, 2002, pp. 1-28.
Biankin, A.V. et al. "Pancreatic cancer genomes reveal aberrations in axon guidance pathway genes." Nature. Nov. 15, 2012; 491(7424): 399-405.
Catalogue of somatic mutations in cancer (COSMIC). Cosmic gene overview: SF3B1. Wellcome Trust Sanger Institute, Genome Research Limited. 1 page, downloaded May 1, 2015. http://cancer.sanger.ac.uk/cosmic/gene/overview?ln=SF3B1.
Damm, F. et al. "SF3B1 mutations in myelodysplastic syndromes: clinical associations and prognostic implications." Leukemia. 2012; 26: 1137-1140.
Darman, R.B. et al. (Nov. 3, 2015) "Cancer-Associated SF3B1 Hotspot Mutations Induce Cryptic 3' Splice Site Selection through Use of a Different Branch Point." Cell Reports, 13(5):1033-1045.
David, C.J. and Manley, J.L. (2010) "Alternative pre-mRNA splicing regulation in cancer: pathways and programs unhinged." Genes & Development, 24:2343-2364.
Deboever, C. et al. "Transcriptome Sequencing Reveals Potential Mechanism of Cryptic 3' Splice Site Selection in SF3B1-Mutated Cancers." PLOS Computational Biology. Mar. 13, 2015; DOI:10.1371/journal.pcbi.1004105: 1/19.
Dvinge, H. et al. (2016) "RNA splicing factors as oncoproteins and tumour suppressors." Nature Reviews Cancer, 16(7):413-430.
Ellis, M.J. et al. "Whole-genome analysis informs breast cancer response to aromatase inhibition." Nature. Jun. 21, 2012; 486: 353-360.
Eskens, F. A.L.M. et al. "Phase 1 Pharmacokinetic and Pharmacodynamic Study of the First-in-Class Spliceosome Inhibitor E7107 in Patients with Advanced Solid Tumors." Cancer Therapy: Clinical. Nov. 15, 2013; 19(22): 6296-304.
Furney, S.J. et al. "SF3B1 Mutations are Associated with Alternative Splicing in Uveal Melanoma. Cancer Discovery." Oct. 2013; 3(10): 1122-9.
H3 Biomedicine Inc. (May 11, 2016) Press release: "H3 Biomedicine Receives FDA Acceptance for Investigational New Drug Application Novel Hematologic Compound Bolsters Company's Emerging Drug Pipeline" [online]. Retrieved from: https://www.h3biomedicine.com/2016/05/11/biomedicine-receives-fda-acceptance-for-investigational-new-drug-application-novel-hematologic-compound-bolsters-companys-emerging-drug-pipeline/; on Aug. 8, 2016 (3 pages).
Hong, D.S. et al. (2014) "A phase I, open-label, single-arm, dose-escalation study of E7107, a precursor messenger ribonucleic acid (pre-mRNA) spliceosome inhibitor administered intravenously on days 1 and 8 every 21 days to patients with solid tumors." Invest New Drugs, 32:436-444.
International Search Report and Written Opinion, PCT/US2015/030464, dated Jul. 21, 2015.
Je, E.M. et al. "Mutational analysis of splicing machinery genes SF3B1, U2AF1 and SRSF2 in myelodysplasia and other common tumors." International Journal of Cancer. Feb. 5, 2013; 133: 260-266.
Kanada, R.M. et al. "Total Synthesis of the Potent Antitumor Macrolides Pladienolide B and D." Angew. Chem. Int. Ed. 2007; 46: 4350-4355.
Kar, S.A. et al. "Spliceosomal gene mutations are frequent events in the diverse mutational spectrum of chronic myelomonocytic leukemia but largely absent in juvenile myelomonocytic leukemia." Haematologica. Jan. 2013; 98: 107-117.
Kim, E. et al. (May 11, 2015) "SRSF2 Mutations Contribute to Myelodysplasia by Mutant-Specific Effects on Exon Recognition." Cancer Cell, 27(5):617-630.
Kotake, Y. et al. "Splicing factor SF3b as a target of the antitumor natural product pladienolide." Nature Chemical Biology. vol. 3, No. 9, Sep. 2007, pp. 570-575.
Maciejewski, J.P. and Padgett, R.A. "Defects in spliceosomal machinery: a new pathway of leukaemogenesis." British Journal of Haemotology. 2012; 158: 165-173.
Madan, V. et al. (2015) "Aberrant splicing of U12-type introns is the hallmark of ZRSR2 mutant myelodysplastic syndrome." Nat. Commun, 6:6042 doi: 10.1038/ncomms7042. HHS Public Access Author Manuscript; available in PMC Jul. 14, 2015 [online]. Retrieved from: http://www.ncbi.nlm.nih.gov/pmc/articles/PMC4349895/ (32 pages).
Maguire, S.L. et al. "SF3B1 mutations constitute a novel therapeutic target in breast cancer." Journal of Pathology. 2015; 235: 571-580.
Makishima, H. et al. "Mutations in the spliceosome machinery, a novel and ubiquitous pathway in leukemogenesis." Blood. Apr. 5, 2012; 119(14): 3203-3210.
Malcovati, L. et al. "Clinical significance of SFB1 mutations in myelodysplastic syndromes and myelodysplastic/myeloproliferative neoplasms." Blood. Dec. 8, 2011; 118(24); 6239-6246.
Neidle, S, ed. Cancer Drug Design and Discovery, (Elsevier/Academic Press, 2008), pp. 427-431.
Papaemmanuil, E. et al. "Somatic SFB1 Mutation in Myelodysplasic with Ring Sideroblasts." The New England Journal of Medicine. Oct. 13, 2011; 365(15): 1384-1395.
Quesada, V. et al. "Exome sequencing identifies recurrent mutations of the splicing factor SF3B1 gene in chronic lymphocytic leukemia." Nature Genetics. Jan. 2012; 44(1): 47-52.
Rossi, D. et al. "Mutations of the SF3B1 splicing factor in chronic lymphocytic leukemia; association with progression and fludarabine-refractoriness." Blood. Dec. 22, 2011; 118(26): 6904-6908.
Sakai, T. et al. "Pladienolides, New Substances from Culture of *Streptomyces platensis* Mer-11107." I. Taxonomy, Fermentation, Isolation and Screening. The Journal of Antibiotics. Mar. 2004; 57(3): 173-179.
Sakai, T. et al. Pladienolides, New Substances from Culture of *Streptomyces platensis* Mer-11107. II. Physico-chemical Properties and Structure Elucidation. The Journal of Antibiotics. Mar. 2004; 57(3): 180-187.
Scott LM and Rebel VI. Acquired mutations that affect pre-mRNA splicing in hematologic malignancies and solid tumors. J Natl Cancer Inst. Oct. 16, 2013: 105(20): 1540-1549.
Shirai, C.L. et al. (May 11, 2015) "Mutant U2AF1 Expression Alters Hematopoiesis and Pre-mRNA Splicing In Vivo" Cancer Cell, 27(5):631-643.
Tefferi A and Vardiman JW. Myeloplastic syndomes. New England Journal of Medicine. Nov. 5, 2009; 361(19): 1872-85.

(56) References Cited

OTHER PUBLICATIONS

Voskoglou-Nomikos, T. et al. (Sep. 15, 2003) "Clinical Predictive Value of the in Vitro Cell Line, Human Xenograft, and Mouse Allograft Preclinical Cancer Models" *Clin Cancer Res*, 9(11):4227-4239.

Wang, L. et al. SF3B1 and Other Novel Cancer Genes in Chronic Lymphocytic Leukemia; The New England Journal of Medicine, Dec. 29, 2011. © 2011 Massachusetts Medical Society; Downloaded from nejm.org at Harvard University on Apr. 27, 2012; pp. 2497-2506.

Yokoi A. et al. Biological validation that SF3b is a target of the antitumor macrolide pladienolide. FEBS Journal. 2011; 278; 4870-4880.

Yoshida K et al. Frequent pathway mutations of splicing machinery in myelodysplasia. Nature. Oct. 2011; 478; 64-69.

Yoshida, K. and S. Ogawa (2014) "Splicing factor mutations and cancer" *WIREs RNA*, 5:445-459.

J. Bernstein, "Polymorphism in Molecular Crystals", Clarendon Press, pp. 240-242, 2002.

B. Moulton et al., "Chemical Reviews", vol. 101, No. 6, pp. 1629-1658, 2001.

Search Report for Russian Application No. 2018121610. (2 pages); and translation (2 pages).

\* cited by examiner

CRYSTALLINE FORM OF (2S,3S,6S,7R,10R,E)-7,10-DIHYDROXY-3,7-DIMETHYL-12-OXO-2-((R,2E,4E)-6-(PIRIDIN-2-YL)-HEPTA-2,4-DIEN-2-YL)OXACYCLODODEC-4-EN-6-YL-4-METHYLPIPERAZINE-1-CARBOXYLATE AND METHODS OF USE THEREOF

This is a national stage application under 35 U.S.C. § 371 of International Application No. PCT/US2016/062525, filed Nov. 17, 2016, which designated the U.S. and which claims the benefit of U.S. Provisional Application No. 62/257,088, filed Nov. 18, 2015, all of which are incorporated herein by reference.

The present disclosure provides a novel solid state form of pladienolide pyridine compounds, compositions comprising at least one such solid state form, and methods of preparation and use of the same. The novel solid state form of pladienolide pyridine compounds may be useful in the treatment of cancer, such as, for example, cancers in which agents that target the spliceosome and mutations therein are known to be useful.

Certain pladienolide B compounds, as well as other pladienolide compounds, are disclosed the following patent applications: WO 2002/060890; WO 2004/011459; WO 2004/011661; WO 2004/050890; WO 2005/052152; WO 2006/009276; and WO 2008/126918. For example, a pladienolide compound, (8E,12E,14E)-7-((4-cycloheptylpiperazin-1-yl)carbonyl)oxy-3,6,16,21-tetrahydroxy-6,10,12,16,20-pentamethyl-18,19-epoxytricosa-8,12,14-trien-11-olide, also known as E7107, is a semisynthetic derivative of the natural product pladienolide D, and the results of its Phase I study have been reported.

The present disclosure provides a novel solid state form of at least one entity chosen from pladienolide pyridine compounds having Formula I and pharmaceutically acceptable salts thereof (collectively "Compounds of Formula I"):

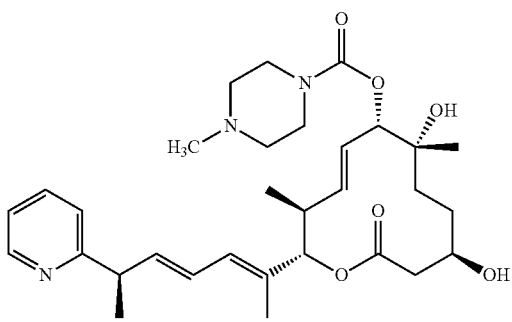

Formula I

In some embodiments, the solid state form of at least one Compound of Formula I is crystalline Form 1. In some embodiments, the present disclosure provides a novel solid state form of (2S,3S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate.

In some embodiments, the present disclosure is directed to pharmaceutical compositions comprising at least one solid state form of at least one Compound of Formula I. In some embodiments, pharmaceutical compositions further comprise at least one additional component chosen from pharmaceutically acceptable carriers, pharmaceutically acceptable vehicles, and pharmaceutically acceptable excipients. In some embodiments, the present disclosure is directed to pharmaceutical compositions consisting of at least one solid state form of at least one Compound of Formula I and optionally at least one additional component. In some embodiments, the present disclosure is directed to pharmaceutical compositions consisting essentially of at least one solid state form of at least one Compound of Formula I and optionally at least one additional component. In some embodiments, the at least one solid state form of at least one Compound of Formula I is present in a pharmaceutical composition in a therapeutically effective amount.

In some embodiments, the at least one solid state form of at least one Compound of Formula I may be used in methods for treating a subject with cancer. In some embodiments, the at least one solid state form of at least one Compound of Formula I may be administered to such a subject in an amount effective to produce a therapeutically beneficial response. Non-limiting examples of cancer include myelodysplastic syndrome, leukemia (such as, for example, chronic lymphocytic leukemia, acute lymphoblastic leukemia, chronic myelomonocytic leukemia, and acute myeloid leukemia), and solid tumors (such as, for example, colon cancer, pancreatic cancer, endometrial cancer, ovarian cancer, breast cancer, uveal melanoma, gastric cancer, cholangiocarcinoma, and lung cancer). The cancer may test positive for one or more mutations in a spliceosome gene or protein, such as those listed in Table 1 below.

In some embodiments, the at least one solid state form of at least one Compound of Formula I may be useful in the preparation of a medicament. For example, the medicament may be for the treatment of cancer, such as those disclosed above. In some embodiments, the at least one solid state form of at least one Compound of Formula I may be useful to target a spliceosome, e.g., subunit 1 of the SF3B spliceosome.

Figure 1:
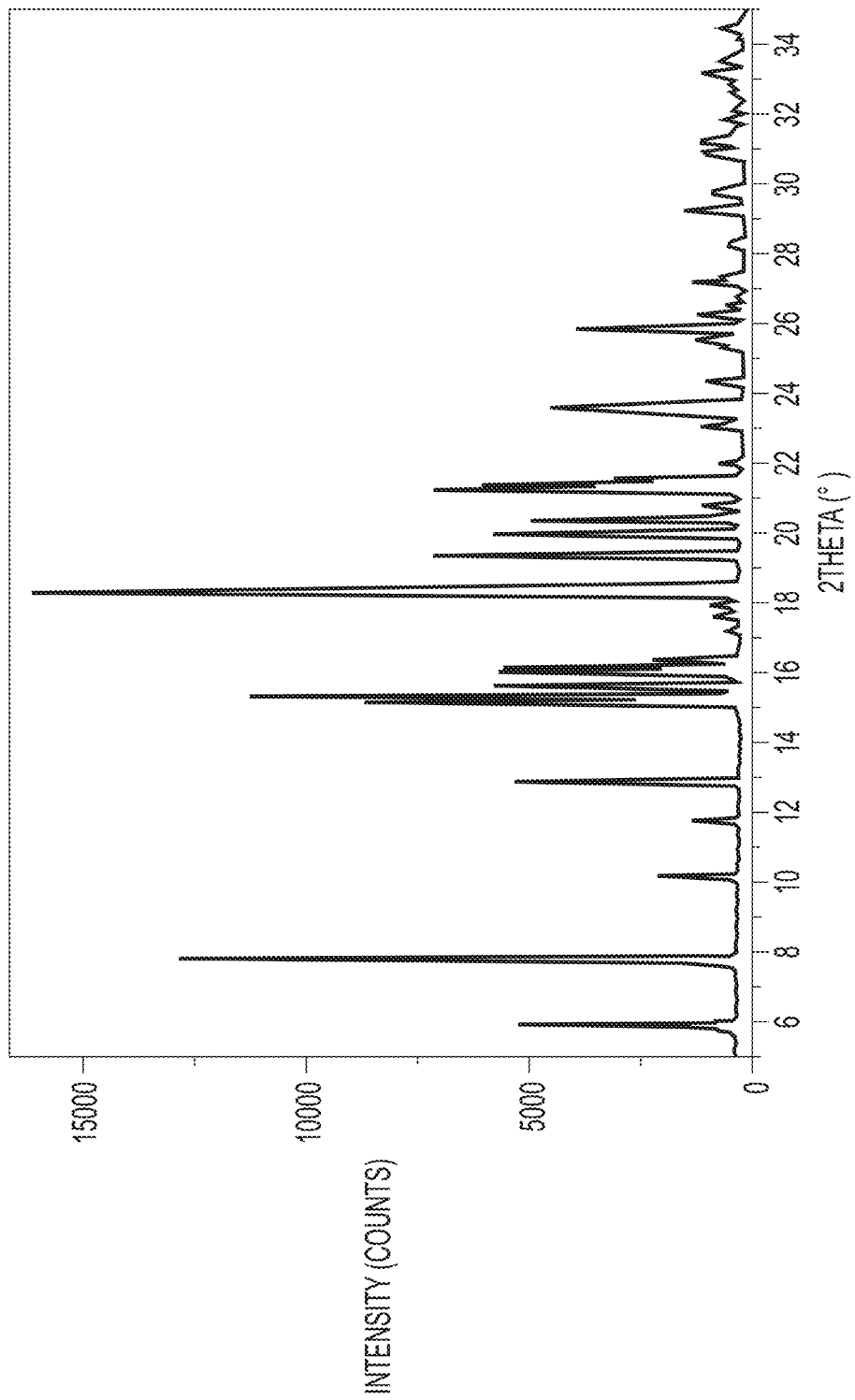
FIG. 1 shows an X-Ray Powder Diffraction (XRPD) diffractogram of crystalline Form 1 of the free base compound of Formula I.

As used herein, the following definitions shall apply unless otherwise indicated.

As used herein, "Compound of Formula I" means at least one entity chosen from compounds of Formula I and pharmaceutically acceptable salts thereof. Furthermore, unless otherwise stated, "Compounds of Formula I" may be one or more of the enantiomeric, diastereomeric, and/or geometric (or conformational) forms of the compound(s); for example, the R and S configurations for each asymmetric center, (Z) and (E) double bond isomers, and (Z) and (E) conformational isomers. Unless otherwise stated, compounds depicted herein coexisting with tautomeric forms are within the scope of the disclosure. Additionally, unless otherwise stated, structures depicted herein are also meant to include compounds that differ only in the presence of one or more isotopically enriched atoms. For example, compounds having the depicted structures except for the replacement of hydrogen by deuterium or tritium, or the replacement of a carbon by a $^{13}$C- or $^{14}$C-enriched carbon are within the scope of this disclosure. Such compounds may be useful, for example, as analytical tools or probes in biological assays.

Formula I may be represented by the following:

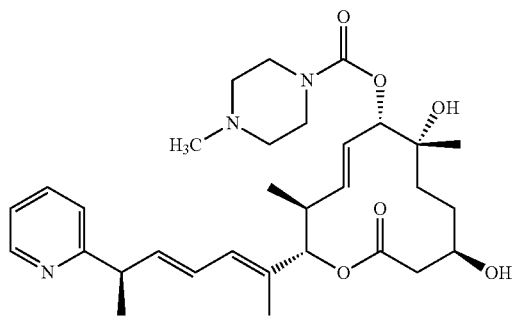 [SMILES: C/C(=C\C=C\[C@@H](C)c1ccccn1)[C@H]1OC(=O)C[C@H](O)CC[C@@](C)(O)[C@@H](OC(=O)N2CCN(C)CC2)/C=C/[C@@H]1C]

A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes et al., "Commentary: Occurrence of Pharmaceutically Acceptable Anions and Cations in the Cambridge Structural Database," *J. Pharmaceutical Sciences*, vol. 94, no. 10 (2005), and Berge et al., "Pharmaceutical Salts," *J. Pharmaceutical Sciences*, vol. 66, no. 1 (1977), which are incorporated by reference herein.

"Solid state form" refer to amorphous or crystalline form of Compounds for Formula I. In some embodiments, the solid state form of at least one Compound of Formula I is crystalline Form 1. The solid state forms can be identified and distinguished from each other by one or more analytical tests and/or physical properties such as, for example, X-ray powder diffraction (XRPD) diffractograms, single crystal structure, heat flow information from differential scanning calorimetry (DSC), absorption-desorption plots from dynamic vapor sorption (DVS), and/or thermodynamic stability. One of ordinary skill in the art will understand, however, that results from such analytical techniques may vary due to experimental error, such as by ±10%. For example, there may be variation in the intensities and/or peak positions in XRPD diffractograms even for the same crystalline form. Thus, those or ordinary skill in the art will understand that the peak maximum values in XRPD diffractograms (in degrees two-theta) referred to herein generally mean that value reported ±0.2 degrees two-theta of the reported value, an art-recognized variance.

"Isomers" refers to compounds having the same number and kind of atoms, and hence the same molecular weight, but differing with respect to the arrangement or configuration of the atoms. "Stereoisomers" refers to compounds that have the same atomic connectivity but different arrangements of their atoms in space. "Diastereoisomers" or "diastereomers" refers to stereoisomers that are not enantiomers. "Enantiomers" refers to stereoisomers that are non-superimposable mirror images of one another. "Geometric isomers" refers to cis-trans isomers having different positions of groups with respect to a double bond or ring or central atom.

Enantiomers taught herein may include "enantiomerically pure" isomers that comprise substantially a single enantiomer, for example, greater than or equal to 90%, 92%, 95%, 98%, or 99%, or equal to 100% of a single enantiomer, at a particular asymmetric center or centers. An "asymmetric center" or "chiral center" refers to a tetrahedral carbon atom that comprises four different substituents.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the opposite enantiomer, of the compound. A typical stereomerically pure compound comprises greater than about 80% by weight of one stereoisomer of the compound and less than about 20% by weight of the other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Pharmaceutically acceptable carrier" as used herein refers to a nontoxic carrier, adjuvant, and/or vehicle that does not destroy the pharmacological activity of the compound with which it is formulated. Pharmaceutically acceptable carriers, adjuvants and/or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol, and wool fat.

"Treatment," "treat," or "treating" cancer refers to reversing (e.g., overcoming a differentiation blockage of the cells), alleviating (e.g., alleviating one or more symptoms, such as fatigue from anemia, low blood counts, etc.), and/or delaying the progression of (e.g., delaying the progression of the condition such as transformation to AML) a cancer as described herein.

"Subject," as used herein, means an animal subject, such as a mammalian subject, and for example, a human being.

In some embodiments, the solid state form of at least one Compound of Formula I is crystalline Form 1.

Amorphous forms of pharmaceutically acceptable salts of compounds of Formula I can be obtained, for example, by combining at least one free base compounds of Formula I with a solvent system comprising at least one acid chosen from phosphoric acid, sulfuric acid, hydrochloric acid, hydrobromic acid, acetic acid, and methanesulfonic acid, and optionally further comprising water. The amorphous form of the free base compound of Formula I can be obtained, for example, from slow evaporation of solutions containing the free base compound of Formula I and at least one solvent chosen from methanol, tetrahydrofuran, acetonitrile, and isopropyl alcohol. Slow evaporation may involve loosely capping a vial comprising solution to be evaporated and allowing the at least one solvent to evaporate at room temperature for about 3 days or as necessary. In some embodiments, the free base compound of Formula I is present in an amount of about 1-2 mg and the at least one solvent is present in a volume of about 2 mL prior to evaporation.

Figure 2:
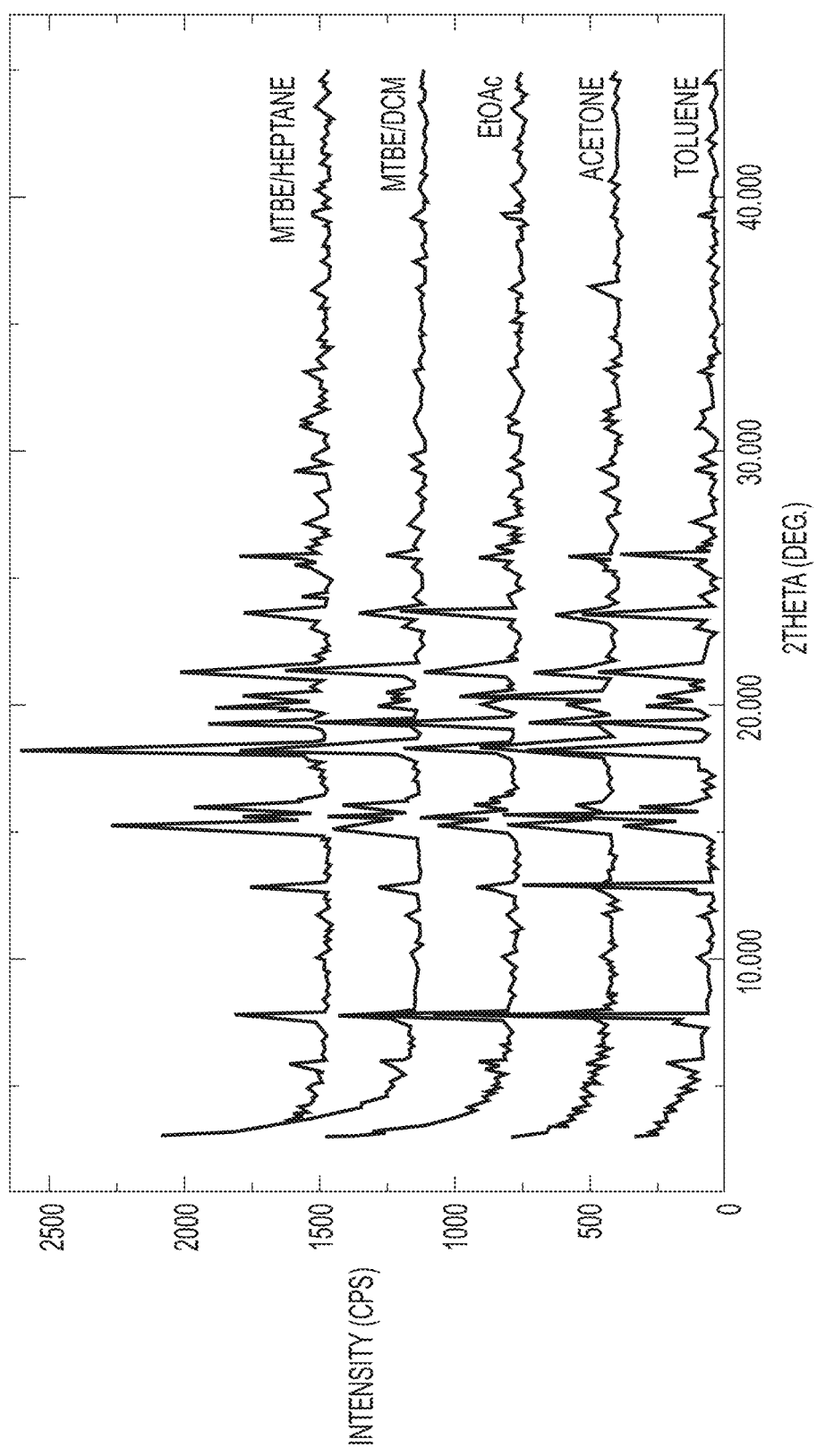
FIG. 2 shows XRPD diffractograms of crystalline Form 1 of the free base compound of Formula I obtained by slow evaporation of various solutions containing toluene, acetone, ethyl acetate, methyl tert-butyl ether (MTBE)/dichloromethane (DCM), or MTBE/heptane.

In some embodiments, crystalline Form 1 of the free base compound of Formula I can be obtained, for example, from slow evaporation (e.g., as previously described) of solutions containing the free base compound of Formula I and at least one solvent chosen from toluene, acetone, ethyl acetate, and a 9:1 (v/v) mixture of MTBE/DCM. In some embodiments, the free base compound of Formula I is present in an amount of about 5 mg and the at least one solvent is present in a volume of about 5 mL prior to evaporation. The XRPD diffractograms of the products obtained from slow evaporation of the above-mentioned solvents are shown in FIG. 2.

Figure 3:
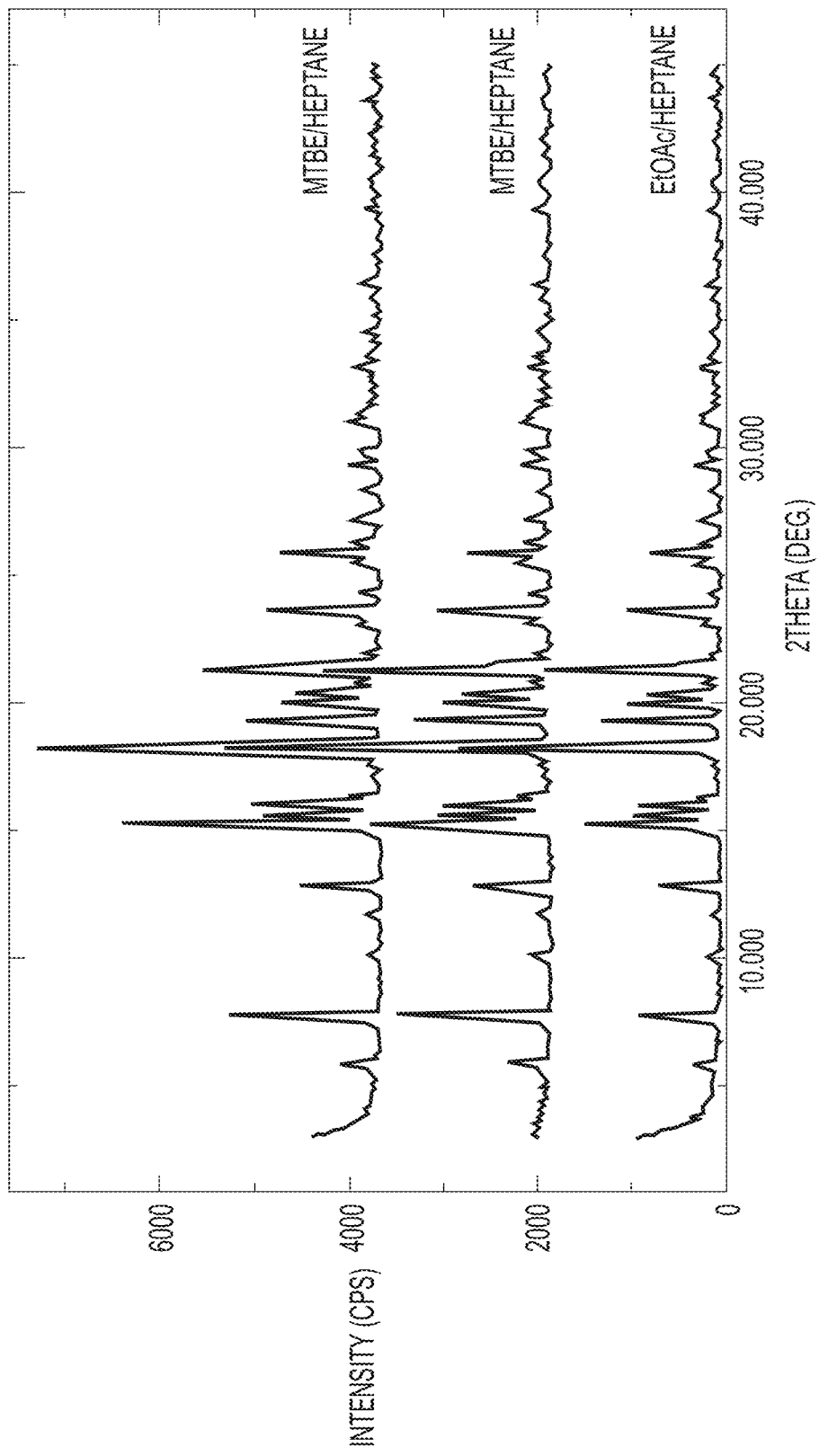
FIG. 3 shows XRPD diffractograms of crystalline Form 1 of the free base compound of Formula I obtained from mixtures of MTBE/heptane or of ethyl acetate/heptane.

Similarly, crystalline Form 1 of the free base compound of Formula I can be obtained, for example, from slow cooling of solutions containing the free base compound of Formula I and either a 1:1 (v/v) mixture of MTBE/heptane or a 1:1 (v/v) mixture of ethyl acetate/heptane from about 50° C. to room temperature over a period of about 20 minutes, followed by cooling to −5° C., and collection by filtration. In some embodiments, the free base compound of Formula I is present in an amount ranging from about 0.2 g to about 9 g and the at least one solvent is present in a volume ranging from about 12v to about 14v (about 8 mL to about 172 mL total solvent volume). The XRPD diffractograms of the products obtained from slow evaporation of the above-mentioned solvents are shown in FIG. 3.

Crystalline Form 1 of the free base compound of Formula I also can be obtained, for example, from slow evaporation of solutions containing the free base compound of Formula I and at least one solvent system chosen from a solution of 5% methanol in ethyl acetate, a solution of 5% methanol in MTBE, a solution of 5% methanol in 1:1 (v/v) MTBE/heptane, a solution of 5% methanol in 1:1 (v/v) ethyl acetate/heptane, a solution of 5% ethanol in ethyl acetate, a solution of 5% ethanol in MTBE, a solution of 5% ethanol in 1:1 (v/v) MTBE/heptane, and a solution of 5% ethanol in 1:1 (v/v) ethyl acetate/heptane. In some embodiments, the free base compound of Formula I is present in an amount of about 0.5 mg and the at least one solvent is present in a volume of about 1 mL.

Figure 4:
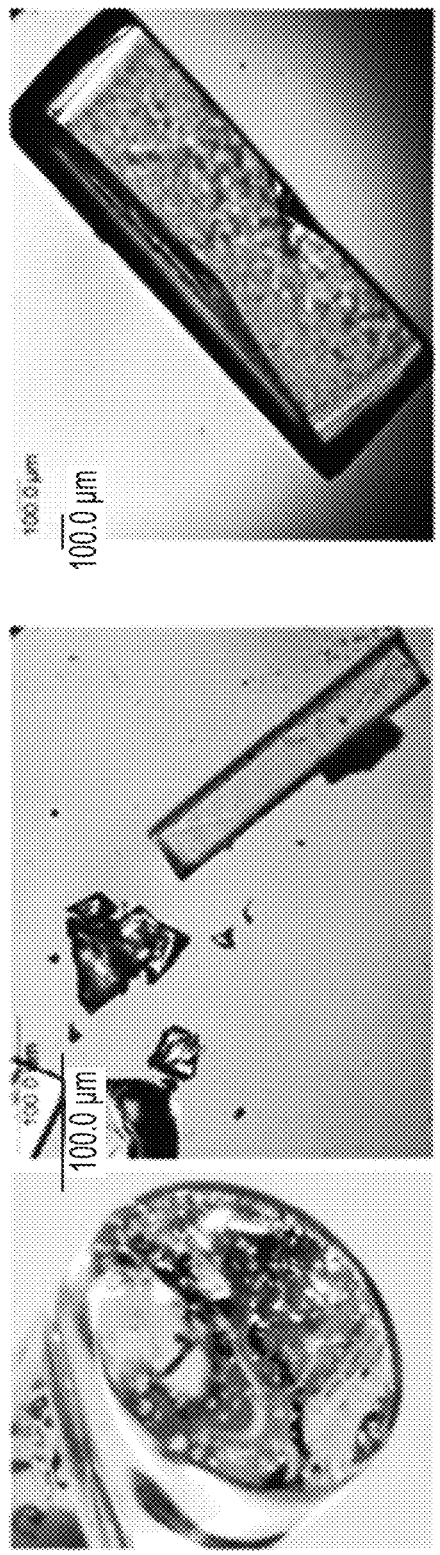
FIG. 4 shows crystals of crystalline Form 1 obtained from fast cooling of the free base compound of Formula I from mixtures of MTBE/heptane or of ethyl acetate/heptane.
Figure 5:
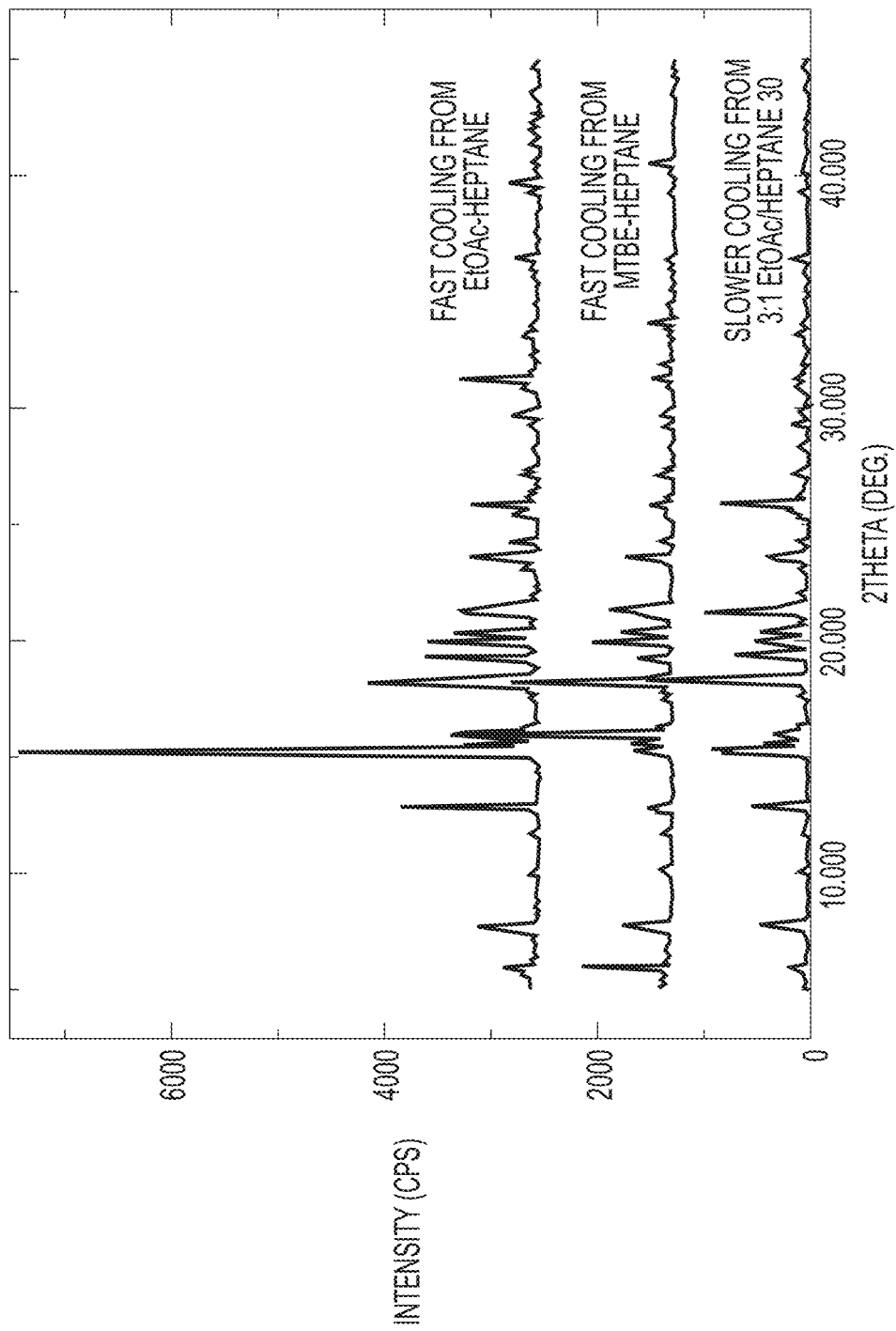
FIG. 5 shows XRPD diffractograms of crystalline Form 1 obtained from different methods. The top diffractogram is of crystalline Form 1 formed by fast cooling from an ethyl acetate/heptane (3:1) solution. The middle diffractogram is of crystalline Form 1 formed by fast cooling from an MTBE/heptane (1:1) solution. The bottom diffractogram is of crystalline Form 1 formed by slower cooling crystallization (cooled from 75° C. to room temperature over 2-3 hours then stirred overnight) from an ethyl acetate/heptane (3:1) solution (30 v).

Crystalline Form 1 of the free base of compound of Formula I can also be obtained, for example, from crash (fast) cooling as described below of solutions containing the free base compound of Formula I and at least one solvent system chosen from 1:1 (v/v) MTBE/heptane and 1:1 (v/v) ethyl acetate/heptane. Crash (fast) cooling may involve increasing the temperature of the solution to 80° C., maintaining that temperature for 10 minutes, and then putting the solution into a freezer at −20° C. After 30 minutes, the mixture may be taken out of the freezer, and solids isolated by filtration. In some embodiments, the free base compound of Formula I is present in an amount of about 3.9 g and the at least one solvent is present in a volume of about 105 mL. For analysis, the solid as well as small amount of the solution may be spread on an XRPD sample plate to allow the solvent to be evaporated (e.g., for 1 hour) at room temperature. Crystals obtained and XRPD diffractograms of the products obtained from crash (fast) cooling of the above-mentioned solvents, and subsequent filtration, are shown in FIGS. 4 and 5 respectively.

Slow evaporation of crystals from MTBE (1% water in MBTE, as measured by KF) or from water-saturated MTBE/heptane did not result in conversion from Form 1 to amorphous or a different crystalline form.

In some embodiments, the present disclosure is drawn to crystalline Form 1 of the free base of compound of Formula I. In some embodiments, the present disclosure relates to crystalline Form 1 having an X-ray powder diffractogram substantially as shown in any one of FIGS. 1, 2, 3, and 5. As used herein, an X-ray powder diffractogram is "substantially as shown" in one or more of the figures herein when it is the same as that in the figure(s) taking into account possible variations in peak positions due to experimental variances and also due to measurement conditions employed, but not taking into account the magnitude (quantitative or relative) intensity of the peaks.

In some embodiments, the XRPD diffractogram of crystalline Form 1 has at least one, at least two, at least three, at least four, at least five, at least six, at least seven, at least eight, or nine peaks chosen from peaks having a maximum at 5.869, 7.749, 12.837, 15.276, 18.220, 19.925, 21.184, 23.586, and 25.817 degrees two-theta (or values rounded therefrom. In some embodiments, a variance of ±0.2(00) may be observed in one or more of the peak maxima.

In some embodiments, the XRPD diffractogram of crystalline Form 1 has at least one, at least two, at least three, at least four, at least five, at least six, at least seven, at least eight, or nine peaks chosen from peaks having a maximum at 5.9, 7.7, 12.8, 15.3, 18.2, 19.3, 21.2, 23.6, and 25.8 degrees two-theta. In some embodiments, a variance of ±0.2 may be observed in one or more of the peak maxima. In some embodiments, the XRPD diffractogram of crystalline Form 1 has at least one, at least two, at least three, at least four, at least five, at least six, at least seven, at least eight, or nine peaks chosen from peaks having a maximum at 5.87, 7.75, 12.84, 15.28, 18.22, 19.29, 21.18, 23.59, and 25.82 degrees two-theta. In some embodiments, a variance of ±0.20 may be observed in one or more of the peak maxima. In some embodiments, the XRPD diffractogram of crystalline Form 1 has at least one, at least two, at least three, at least four, at least five, at least six, at least seven, at least eight, or nine peaks chosen from peaks having a maximum at 5.869, 7.749, 12.837, 15.276, 18.220, 19.295, 21.184, 23.586, and 25.817 degrees two-theta. In some embodiments, a variance of ±0.200 may be observed in one or more of the peak maxima.

In some embodiments, the XRPD diffractogram of crystalline Form 1 has an XRPD diffractogram which has at least one peak chosen from peaks at 5.9±0.2, 7.7±0.2, 12.8±0.2, 15.3±0.2, 18.2±0.2, 19.3±0.2, 21.2±0.2, 23.6±0.2 and 25.8±0.2 degrees two-theta. In some embodiments, the XRPD diffractogram of crystalline Form 1 has an XRPD diffractogram which has a peak at 18.2±0.2 degrees two-theta. In some embodiments, the XRPD diffractogram of crystalline Form 1 has an XRPD diffractogram which has peaks at 7.7±0.2, 15.3±0.2 and 18.2±0.2 degrees two-theta. In some embodiments, the XRPD diffractogram of crystalline Form 1 has an XRPD diffractogram which has peaks at 7.7±0.2, 15.3±0.2, 18.2±0.2, 19.3±0.2 and 21.2±0.2 degrees two-theta.

In some embodiments, crystalline Form 1 is in space group $P2_1$. In some embodiments, a unit cell of crystalline Form 1 has dimensions: a=5.9306(2) Å, b=17.4304(6) Å, c=15.1800(5) Å, β=99.641(2). In some embodiments, a unit cell of crystalline Form 1 has a volume of 1547.03(9) Å$^3$.

In some embodiments, the present disclosure is directed to pharmaceutical compositions comprising at least one solid state form of at least one Compound of Formula I. In some embodiments, pharmaceutical compositions further comprise at least one additional component chosen from pharmaceutically acceptable carriers, pharmaceutically acceptable vehicles, and pharmaceutically acceptable excipients.

In some embodiments, a solid state form of at least one Compound of Formula I in the pharmaceutical compositions is the amorphous form of at least one Compound of Formula I. In some embodiments, the amorphous form of at least one Compound of Formula I is the amorphous form of at least one pharmaceutically acceptable salt of a compound of Formula I. In some embodiments, the at least one pharmaceutically acceptable salt is chosen from acid addition salts formed with at least one acid chosen from hydrochloric acid, hydrobromic acid, sulfuric acid, phosphoric acid, nitric acid, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, and polygalacturonic acid. In some embodiments, the at least one pharmaceutically acceptable salt is chosen from acid addition salts formed with at least one acid chosen from hydrochloric acid, sulfuric acid, phosphoric acid, acetic acid, and methanesulfonic acid.

In some embodiments, a solid state form of at least one Compound of Formula I in the pharmaceutical compositions is crystalline Form 1 of at least one Compound of Formula I.

In some embodiments, the present disclosure is directed to pharmaceutical compositions consisting of at least one solid state form of at least one Compound of Formula I and optionally at least one additional component. In some embodiments, the pharmaceutical compositions comprise as the active ingredient more than 80% of at least one solid state form of at least one Compound of Formula I. In some embodiments, the pharmaceutical compositions comprise as the active ingredient more than 90% of at least one solid state form of at least one Compound of Formula I. In some embodiments, the pharmaceutical compositions comprise as the active ingredient more than 95% of at least one solid state form of at least one Compound of Formula I. In some embodiments, the pharmaceutical compositions comprise as the active ingredient more than 99% of at least one solid state form of at least one Compound of Formula I.

In some embodiments, the present disclosure is directed to pharmaceutical compositions consisting essentially of at least one solid state form of at least one Compound of Formula I and optionally at least one additional component. The at least one additional component is not at least one Compound of Formula I.

The at least one additional component in the pharmaceutical compositions may be chosen depending upon the route of administration for which the pharmaceutical composition is intended. Non-limiting examples of suitable routes of administration for which the pharmaceutical composition may be used include parenteral, oral, inhalation spray, topical, rectal, nasal, buccal, vaginal and implanted reservoir administration. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the mode of administration is chosen from intravenous, oral, subcutaneous, and intramuscular administration. Sterile injectable forms of the compositions of this disclosure may be, for example, aqueous or oleaginous suspension. These suspensions may be formulated according to techniques known in the art using suitable dispersing or wetting agents and suspending agents known in the art. The sterile injectable preparation may also be a sterile injectable solution or suspension in a nontoxic parenterally acceptable diluent or solvent, for example, as a solution in 1,3-butanediol. Non-limiting examples of vehicles and solvents that may be employed include water, Ringer's solution, and isotonic sodium chloride solution. In addition, sterile, fixed oils may be employed as a solvent and/or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, and/or other dosage forms, may also be used for the purposes of formulation.

For oral administration, the at least one solid state form of at least one Compound of Formula I may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient is combined with an emulsifying and/or suspending agent. If desired, certain sweetening, flavoring or coloring agents may also be added.

The at least one solid state form of at least one Compound of Formula I of the present disclosure may be used to treat various types of cancers, including those responsive to agents that target SF3B1. The anti-tumor activity of pladienolide B is reported as being connected to its targeting of the SF3b complex, inhibiting splicing and altering the pattern of gene expression (Kotake et al., "Splicing factor SF3b as a target of the antitumor natural product pladienolide," Nature Chemical Biology 2007, 3, 570-575). Mutations in spliceosome genes such as the Splicing factor 3B subunit 1 (SF3B1) protein are known to be implicated in a number of cancers, such as hematologic malignancies and solid tumors. Scott et al., "Acquired mutations that affect pre-mRNA splicing in hematologic malignancies and solid tumors," JNCI 105, 20, 1540-1549.

Non-limiting examples of hematological malignancies include cancers of the blood (leukemia) and cancers of the lymph nodes (lymphomas). Non-limiting examples of leukemias include acute lymphoblastic leukemia (ALL), acute myleogenous leukemia (AML), chronic lymphocytic leukemia (CLL), chronic myelogenous leukemia (CML), chronic myelomonocytic leukemia (CMML), acute monocytic leukemia (AMoL), etc. Non-limiting examples of lymphomas include Hodgkin's lymphoma and non-Hodgkin's lymphoma. Non-limiting examples of other hematologic malignancies include myelodysplastic syndrome (MDS).

Non-limiting examples of solid tumors include carcinomas (such as, for example, adenocarcinoma, e.g., breast cancer, pancreatic cancer, prostate cancer, colon and colorectal cancer), lung cancer, gastric cancer, cervical cancer, endometrial cancer, ovarian cancer, cholangiocarcinoma, glioma, and melanoma.

The at least one solid state form of at least one Compound of Formula I of the present disclosure may also be used to treat cancers that may be responsive to agents that target a spliceosome gene or protein other than SF3B1. The following examples are illustrative of some of the cancers that may be responsive to agents that target the spliceosome, and are not meant to limit the scope of the disclosure in any way. Thus, the at least one solid state form of at least one Compound of Formula I of the present disclosure may be administered to subjects to treat a variety of cancers or conditions, such as:

a) Myelodysplastic syndrome (MDS): See, e.g., "SF3B1 mutations in myelodysplastic syndromes: clinical associations and prognostic implications," Damm F. et al. Leukemia, 2011, 1-4; "Frequent pathway mutations in splicing machinery in myelodysplasia," Yoshida K. et al, Nature, 2011, 478, 64-69; "Clinical significance of SF3B1 mutations in myelodysplastic syndromes and myelodysplastic/myeloproliferative neoplasms," Malcovati L. et al., Blood, 2011, 118, 24, 6239-6246; "Mutations in the spliceosome machinery, a novel and ubiquitous pathway 20 in leukemogenesis," Makishima et al, Blood, 2012, 119, 3203-3210; "Somatic SF3B1 mutation in myelodysplasia with ring sideroblasts," Pappaemannuil, E. et al, New England J. Med. 2011, DOI 10.1056/NEJMoa1 103283.

b) Chronic lymphocytic leukemia (CLL): See, e.g., "Defects in the spliceosomal machinery: a new pathway of leukaemogenesis," Maciejewski, J. P., Padgett, R. A., Br. J. Haematology, 2012, 1-9; "Mutations in the SF3B1 splicing factor in chronic lymphocytic leukemia: associations with progression and fludarabine-refractoriness," Rossi et al, Blood, 2011, 118, 6904-6908; "Exome sequencing identifies recurrent mutations of the splicing factor SF3B1 gene in chronic lymphocytic leukemia," Quesada et al, Nature Genetics, 2011, 44, 47-52.

c) Chronic myelomonocytic leukemia (CMML): See, e.g., Yoshida et al, Nature 2011; 30 "Spliceosomal gene mutations are frequent events in the diverse mutational spectrum of chronic myelomonocytic leukemia but largely absent in juvenile myelomonocytic leukemia," Kar S. A. et al, Haematologia, 2012, DOI: 10.3324/haemato1.2012.064048; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105.

d) Acute myeloid leukemia (AML): See, e.g., Malcovati et al., Blood 2011; Yoshida et al, Nature 2011.

e) Breast cancer: See, e.g., "Whole genome analysis informs breast cancer response to aromatase inhibition," Ellis et al., Nature, 2012, 486, 353-360; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105; Maguire et al., "SF3B1 mutations constitute a novel therapeutic target in breast cancer," J Pathol 2015, 235, 571-580.

f) Uveal melanoma: See, e.g., "SF3B1 mutations are associated with alternative splicing in uveal melanoma," Furney et al., Cancer Disc. 2013, 10, 1122-1129; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105.

g) Endometrial cancer: See, e.g., Tefferi et al., "Myelodysplastic syndromes." N Engl J Med. 2009; 361:1872-85.

h) Gastric cancer: See, e.g., Int J Cancer. 2013 July; 133(1):260-5, "Mutational analysis of splicing machinery genes SF3B1, U2AF1 and SRSF2 in myelodysplasia and other common tumors." Je et al.

i) Ovarian cancer: See, e.g., Int J Cancer. 2013 July; 133(1):260-5, "Mutational analysis of splicing machinery genes SF3B1, U2AF1 and SRSF2 in myelodysplasia and other common tumors." Je et al.

j) Biliary Tract cancers such as Cholangiocarcinoma and Pancreatic cancer: See, e.g., Biankin et al., "Pancreatic cancer genomes reveal aberrations in axon guidance pathway genes," Nature 2012, 491,399-405.

k) Lung cancer: See, e.g., "Exome sequencing identifies recurrent mutations of the splicing factor SF3B1 gene in chronic lymphocytic leukemia," Quesada et al., Nature Genetics 44, 47-52 (2012); Scott et al., "Acquired mutations that affect pre-mRNA splicing in hematologic malignancies and solid tumors," JNCI 105, 20, 1540-1549.

In addition, the Catalogue of somatic mutations in cancer (COSMIC) (Wellcome Trust Sanger Institute, Genome Research Limited, England) reports SF3B1 mutations have been found in various types of cancer samples.

In some embodiments, the at least one solid state form of at least one Compound of Formula I of the present disclosure is administered to a subject in an amount that is a treatment and/or therapeutically effective amount. The amount of the at least one solid state form of at least one Compound of Formula I of the present disclosure that may be combined with a carrier material to produce a composition in a single dosage form may vary depending upon the subject treated and the route of administration. In some embodiments, the pharmaceutical compositions are formulated so that a dosage of between 0.01 mg/kg to 100 mg/kg body weight/day of at least one solid state form of at least one Compound of Formula I based on the weight of the free base of Formula I can be administered to a subject receiving these compositions. In some embodiments, the pharmaceutical compositions of the present disclosure comprise 0.01 mg to 50 mg may indicate the subject's cancer is responsive to a method of treatment comprising administration of a compound targeting this protein and/or the spliceosome. Examples of such spliceosome genes include, but are not limited to, those presented in Table 1, below.

TABLE 1

Spliceosome genes and potential diseases affected

| Spliceosome gene | Disease(s) |
| --- | --- |
| Splicing factor 3B subunit 1 (SF3B1) | see above |
| U2 small nuclear RNA auxiliary factor 1 (U2AF1) | MDS, AML, CMML, LUAD, UCEC |
| Serine/arginine-rich splicing factor 2 (SRSF2) | CMML, MDS, PMF, AML |
| | MDS |
| Zinc finger (CCCH type), RNA-binding motif and serine/arginine rich 2 (ZRSR2) | Retinitis Pigmentosa |
| Pre-mRNA-processing-splicing factor 8 (PRPF8) | Myeloid neoplasms |
| U2 Small Nuclear RNA Auxiliary Factor 2 (U2AF2) | MDS, PRAD, COAD |
| Splicing Factor 1 (SF1) | myeloid neoplasms, OV, COAD |
| Splicing factor 3 a subunit 1 (SF3A1) | MDS |
| PRP40 pre-mRNA processing factor 40 homolog B (PRPF40B) | LUAD |
| RNA Binding Motif Protein 10 (RBM10) | COAD |
| Poly(rC) binding protein 1 (PCBP1) | SKCM |
| Crooked neck pre-mRNA splicing factor 1 (CRNKL1) | LUSC |
| DEAH (Asp-Glu-Ala-His) box helicase 9 (DHX9) | STAD |
| Peptidyl-prolyl cis-trans isomerase-like 2 (PPIL2) | SKCM |
| RNA binding motif protein 22 (RBM22) | LUAD |
| Small nuclear ribonucleoprotein Sm D3 (SNRPD3) | GBM, LGG |
| Probable ATP-dependent RNA helicase DDX5 (DDX5) | LUAD |
| Pre-mRNA-splicing factor ATP-dependent RNA helicase DHX15 (DHX15) | DLBCL |
| Polyadenylate-binding protein 1 (PABPC1) | myeloid neoplasms |

Key:
MDS = Myelodysplastic syndrome
AML = Acute Myeloid Leukemia
CMML = Chronic Myelomonocytic Leukemia
LUAD = Lung Adenocarcinoma
UCEC = Uterine Corpus Endometrial Carcinoma
PMF = Progressive Massive Fibrosis
PRAD = Prostate Adenocarcinoma
COAD = Colon Adenocarcinoma
OV = Ovarian Serous Cystadenocarcinoma
SKCM = Skin Cutaneous Melanoma
LUSC = Lung Squamous Cell Carcinoma
STAD = Stomach Adenocarcinoma
GBM = Glioblastoma Multiforme
LGG = Brain Lower Grade Glioma
DLBCL = Diffuse Large B-Cell Lymphoma based on the weight of the free base of Formula I of at least one solid state form of at least one Compound of Formula I. In some embodiments, the pharmaceutical compositions of the present disclosure comprise 0.1 mg to 25 mg of at least one solid state form of at least one Compound of Formula I, based on the weight of the free base of Formula I, such as 5 mg to 40 mg.

The dosage and treatment regimen for any particular patient may also depend upon a variety of factors, including the activity of the specific compound employed, the age, body weight, general health, sex, diet, time of administration, rate of excretion, drug combination, the judgment of the treating physician, and the severity of the particular disease being treated. The weight amount of at least one solid state form of at least one Compound of Formula I of the present disclosure in a composition will also depend upon the particular compound/salt in the composition.

In some embodiments, the cancer is tested for and/or is positive for one or more mutations in a spliceosome gene or protein, wherein the presence of the mutation(s) ("positive")

In some embodiments, the subject's cancer may be responsive to a method of treatment comprising administration of at least one solid state form of at least one Compound of Formula I targeting this protein and/or the spliceosome even in the absence of such mutations in a spliceosome gene or protein.

Screening or testing for the mutations may be carried out by any known means, for example, genotyping, phenotyping, etc., by way of nucleic acid amplification, electrophoresis, microarrays, blot, functional assays, immunoassays, etc. Methods of screening may include, for example, collecting a biological sample from said subject containing the cancerous cells/tissue.

In order that the disclosure described herein may be more fully understood, the following examples are set forth. It should be understood that these examples are for illustrative purposes only and are not to be construed as limiting this disclosure in any manner.

EXAMPLES

Microwave heating was done using a Biotage Emrys Liberator or Initiator microwave. Column chromatography was carried out using an Isco Rf200d. Solvent removal was carried out using either a Büchi rotary evaporator or a Genevac centrifugal evaporator. Preparative LC/MS was conducted using a Waters autopurifier and 19×100 mm XTerra 5 micron MS C18 column under acidic mobile phase condition. NMR spectra were recorded using a Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like).

General methods and experimental details for preparing Compounds of Formula I of the present disclosure are set forth below.

The following abbreviations are used herein:

MeOH: Methanol

DMF: Dimethylformamide

KHMDS: Potassium bis(trimethylsilyl)amide

LCMS: Liquid chromatography—mass spectrometry

TBS Cl: tert-Butyldimethylsilyl chloride

THF: Tetrahydrofuran

TLC: Thin-layer chromatography

Materials: The following compounds are commercially available and/or can be prepared in a number of ways well known to one skilled in the art of organic synthesis. Compounds of Formula I can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions are apparent to one skilled in the art, and alternate methods are therefore indicated. The starting materials for the examples are either commercially available or are readily prepared by standard methods from known materials.

LCMS Information

Mobile phases: A (0.1% formic acid in $H_2O$) and B (0.1% formic acid in acetonitrile).

Gradient: B 5%→95% in 1.8 minutes.

Column: Acquity BEH C18 column (1.7 um, 2.1×50 mm).

U.S. Pat. Nos. 7,884,128 and 7,816,401, both entitled: Process for Total Synthesis of Pladienolide B and Pladienolide D, describe methods known in the art for synthesis of Pladienolide B and D. Synthesis of Pladienolide B and D may also be performed using methods known in the art and described in Kanada et al., "Total Synthesis of the Potent Antitumor 20 Macrolides Pladienolide B and D,"*Angew. Chem. Int. Ed.* 46:4350-4355 (2007). Kanada et al. and PCT application publication WO 2003/099813, entitled: Novel Physiologically Active Substances, describe methods known in the art for the synthesis of E7107 (Compound 45 of WO '813) from Pladienolide D (11107D of WO '813). A corresponding U.S. Pat. No. 7,550,503 to Kotake et al.

Synthesis of (S)-2-(1-((1-phenyl-1H-tetrazol-5-yl)sulfonyl)propan-2-yl)pyridine

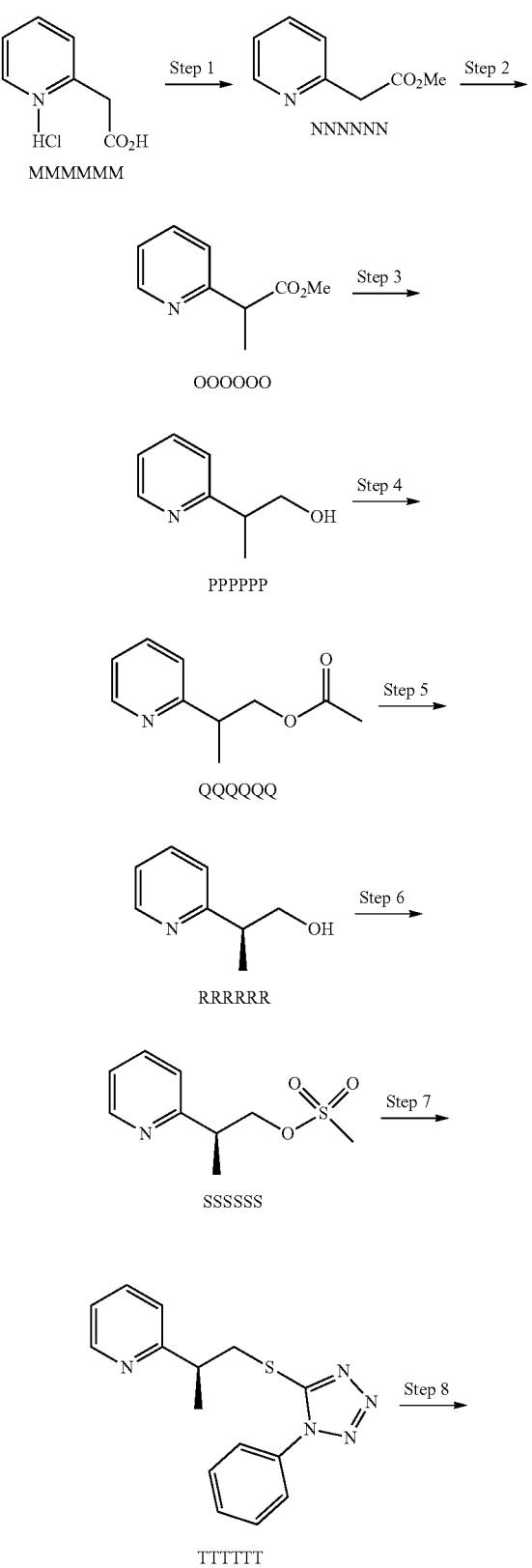

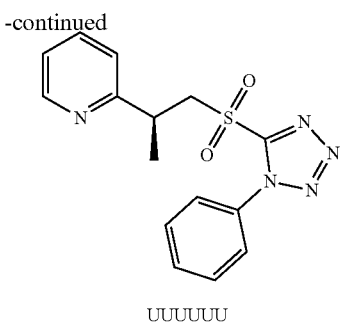

UUUUUU

Step 1: To a solution of 2-(pyridin-2-yl)acetic acid hydrochloride salt MMMMMM (50.0 g, 288.0 mmol, 1.0 equiv.) in methanol (500 mL, 0.5M) at 0° C. was added thionyl chloride (31.5 mL, 432.0 mmol, 1.5 equiv.) dropwise. The reaction was stirred at 0° C. for 60 minutes or until the reaction was determined to be complete by LCMS or TLC. The reaction was carefully quenched with sodium carbonate and the aqueous layer extracted with ethyl acetate. The combined organic layers were washed with water, brine, dried over magnesium sulfate, filtered, and concentrated in vacuo. The resulting product (NNNNNN, 41.5 g, 275.0 mmol, 95%) was used in the next step without further purification.

Step 2: To a solution of ester NNNNNN (41.5 g, 275.0 mmol, 1.0 equiv.) in THF (1500 mL, 0.2M) at 0° C. was added sodium 2-methylpropan-2-olate (28.6 g, 288.3 mmol, 1.05 equiv.) and the reaction mixture was stirred for 30 minutes at 0° C. before addition of iodomethane (34.3 mL, 549.1 mmol, 2.0 equiv.). The reaction was stirred at room temperature for 1 hour or until the reaction was determined to be complete by LCMS or TLC. The reaction was quenched with ammonium chloride and the excess of solvent was removed in vacuo. The crude material was then extracted with ethyl acetate. The combined organic layers were washed with brine, and dried over magnesium sulfate. After filtration, the mixture was concentrated in vacuo. The resulting methyl ester (OOOOOO, 41.3 g, 250 mmol, 91%) was advanced without purification.

Step 3: To a solution of methyl ester OOOOOO (43.0 g, 260.3 mmol, 1.0 equiv.) in THF (1500 mL, 0.1M) at 0° C. was added lithium aluminum hydride (312 mL, 312.4 mmol, 1.2 equiv., solution in THF) dropwise. The reaction was allowed to warm gradually to 0° C. for 30 minutes and then to room temperature for 1 hour or until the reaction was determined to be complete by LCMS or TLC. The reaction was carefully quenched with water, sodium hydroxide and water. After stirring the mixture for 30 minutes, the white precipitate was filtered off and the solvent was removed in vacuo. The reaction was then extracted with diethyl ether and the combined organic fractions were washed with water, brine, dried over magnesium sulfate, filtered, and concentrated in vacuo. The resulting alcohol (PPPPPP, 30.0 g, 219.0 mmol, 84%) was advanced without purification.

Step 4: To a solution of alcohol PPPPPP (30.0 g, 219.0 mmol, 1.0 equiv.) in dichloromethane (700 mL, 0.3M) at 0° C. was added triethylamine (61.5 mL, 437.4 mmol, 2.0 equiv), and DMAP (2.7 g, 21.9 mmol, 0.1 equiv.). Acetic anhydride (24.8 mL, 262.4 mmol, 1.2 equiv.) was added and the reaction mixture was stirred for 30 minutes or until the reaction was determined to be complete by LCMS or TLC. The reaction was quenched with ammonium chloride, the organic layer was washed with brine, dried over magnesium sulfate and filtered. The resulting solution was then evaporated and the crude acetate (QQQQQQ, 37.0 g, 206.0 mmol, 94%) was used in the following step without further purification.

Step 5: A solution of acetate QQQQQQ (39.4 g, 219.8 mmol, 1.0 equiv.) was dissolved in diethyl ether (100 mL) and then 118 g of silica gel was added. The excess of ether was removed in vacuo and the crude solid was then diluted in pH 7 aqueous buffer (1970 mL, 0.1M) (sodium hydroxide/sodium phosphate monobasic/water). Porcine pancreatic lipase type II (3.3 g, (15 mg/mmol)) was added and the reaction was stirred at 37° C. for four hours or until determined to be complete by TLC or LCMS. (After four hours, conversion reached 40% according to ELSD and the enantiomeric excess was determined by chiral SFC, and showed an enantiomeric ratio of 13:1 S:R). (SFC condition: SFC Investigator (Waters/Thar), software: Chromscope v1.2, method: Isocratic 15% co-solvent 95:5 Heptane:IPA+0.1% DEA over 10 minutes, Column: Lux-Amylose-2, 4.6×250 mm, 5 µm, Total Flow: 4 ml/min (3.80 ml from $CO_2$ pump, 0.20 ml from modifier pump), Oven temp set to 35° C. and system pressure set to 100 bar, Retention Times: desired and major (S)-enantiomer 6.9 min, minor (R)-enantiomer 8.4 min). The silica gel was filtered off and the aqueous layer was extracted with ethyl acetate three times. The combined organic layers were washed with brine, dried over magnesium sulfate and concentrated. The product was purified by silica gel column chromatography (hexanes: ethyl acetate as eluant) to afford the desired alcohol (RRRRRR, 12.5 g, 91 mmol, 41%).

Step 6: To a solution of alcohol RRRRRR (12.5 g, 91.0 mmol, 1.00 equiv.) in dichloromethane (570 mL, 0.16M) at room temperature was added triethylamine (13.9 mL, 100.1 mmol, 1.1 equiv). The reaction was cooled down to 0° C. and then methanesulfonyl chloride (7.44 mL, 95.5 mmol, 1.05 equiv) was added. The reaction was stirred at 0° C. for 30 minutes or until determined to be complete by TLC or LCMS. The reaction was quenched with sodium bicarbonate and the layers were separated. The aqueous layer was then extracted with dichloromethane. The combined organic layers were washed with brine, dried over magnesium sulfate, and concentrated in vacuo. The resulting sulfonate SSSSSS (19.2 g, 89 mmol, 98%) was advanced without additional purification.

Step 7: To a solution of sulfonate SSSSSS (19.2 g, 89 mmol, 1.0 equiv.) in DMF (120 mL, 0.1M) at room temperature was added cesium carbonate (40.7 g, 125.0 mmol, 1.4 equiv.) and 1-phenyl-1H-tetrazole-5-thiol (19.1 g, 107.1 mmol, 1.2 equiv.). The resulting mixture was stirred at 50° C. for 48 hours, or until determined to be complete by TLC or LCMS. After cooling the mixture to room temperature, brine was added and the aqueous layer was extracted three times with diethyl ether. The combined organic layers were washed with water, brine, and dried over magnesium sulfate. After filtration, the solvent was removed in vacuo and the residue was purified using silica gel column chromatography (hexanes/ethyl acetate) to give the desired product (TTTTTT, 28.9 g, 88 mmol, 99%).

Step 8: To a solution of sulfide TTTTTT (31.5 g, 105.9 mmol, 1.0 equiv.) in EtOH (700 mL, 0.1M) at −10° C. was added ammonium molybdate tetrahydrate (6.5 g, 5.3 mmol, 0.05 equiv.) and hydrogen peroxide (108 mL, 1060 mmol, 5.0 equiv., 33% aqueous solution). The reaction was stirred at −10° C. for four hours or until determined to be complete by TLC or LCMS. The reaction was quenched with water and sodium metabisulfite solution. The crude product was collected by filtration and was purified by silica gel column chromatography (hexanes:ethyl acetate as eluant) to afford the desired product (UUUUUU, 23.2 g, 70.4 mmol, 66%). $^1$H NMR (400 MHz, CHLOROFORM-d) δ: 1.50 (d, J=7.03 Hz, 3H) 1.66 (br. s., 1H) 3.75 (m, 1H) 3.94 (dd, J=14.81, 5.02 Hz, 1H) 4.55 (dd, J=14.68, 7.91 Hz, 1H) 7.14-7.22 (m, 2H) 7.29 (s, 1H) 7.57-7.70 (m, 6H) 8.44-8.49 (m, 1H).

The colorless oil was then recrystallized using toluene/heptane (1/1) (1 mL of toluene and 1 mL of heptane per 100 mg of compound. Heat gently the mixture to mix the two solvents. Let the mixture cool down to room temperature for 12h. (If no recrystallization is observed, add one crystal to the solution. The crystal will help to get crystals via seeding process.) The crystals formed slowly over time. They could be isolated via filtration or removing liquid layer via pipette. The crystals were then washed with heptane and then quickly with toluene. The er of the sulfone was analyzed before and after recrystallization. (SFC conditions: SFC condition: SFC Investigator (Waters/Thar), software: Chromscope v1.2, method: Isocratic 10% co-solvent MeOH over 10 minutes, Column: ChiralPak IC, 4.6×250 mm, Sum, Total Flow: 4 ml/min (3.80 ml from $CO_2$ pump, 0.20 ml from modifier pump), Oven temp set to 35° C. and system pressure set to 100 bar, Retention Times: desired and major (S)-enantiomer 3.5 min, minor (R)-enantiomer 3.8 min).

Exemplary Synthesis of Compound 1

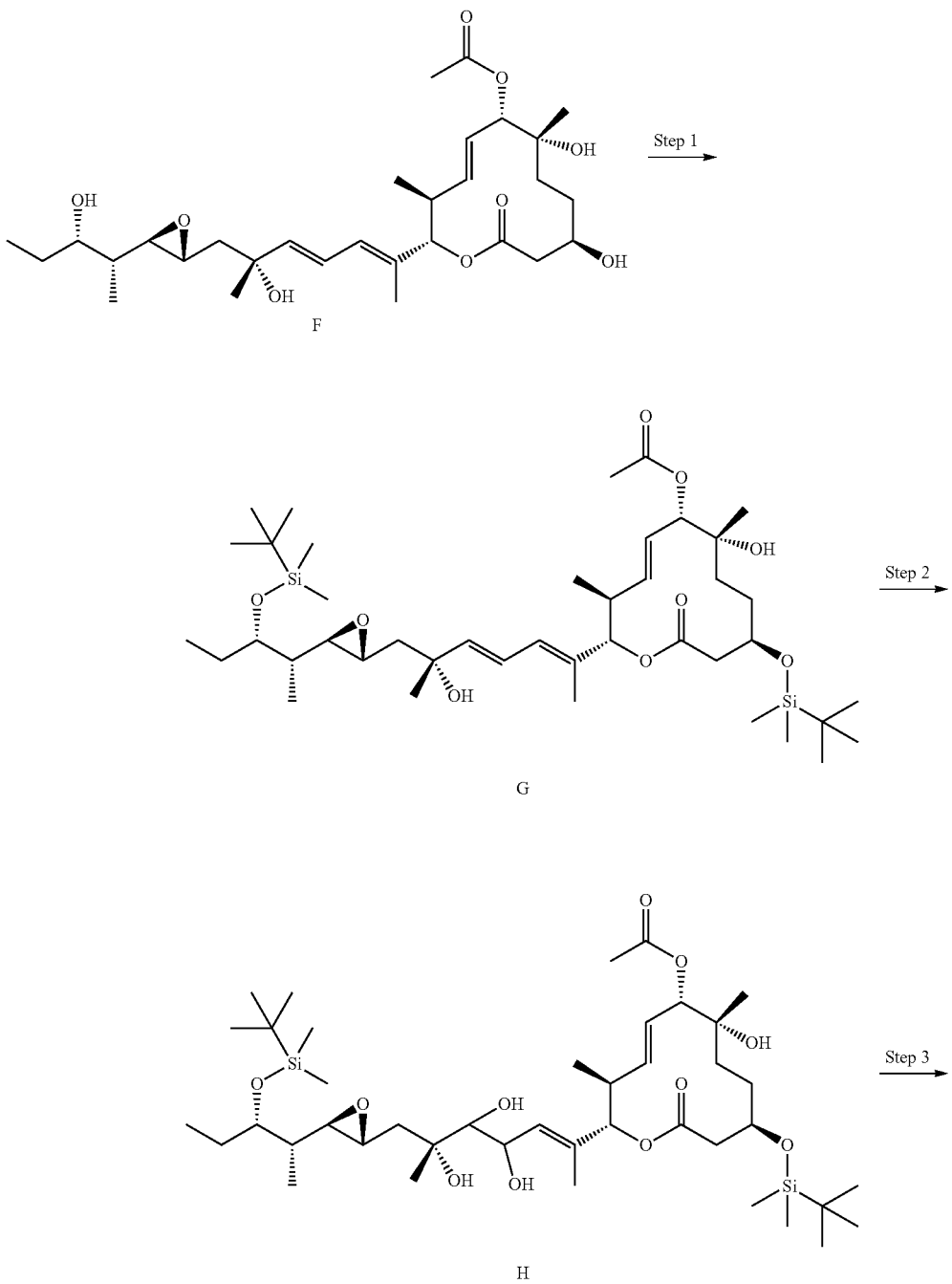

-continued
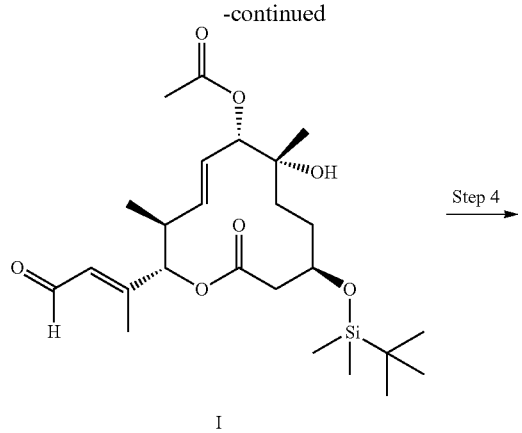
I
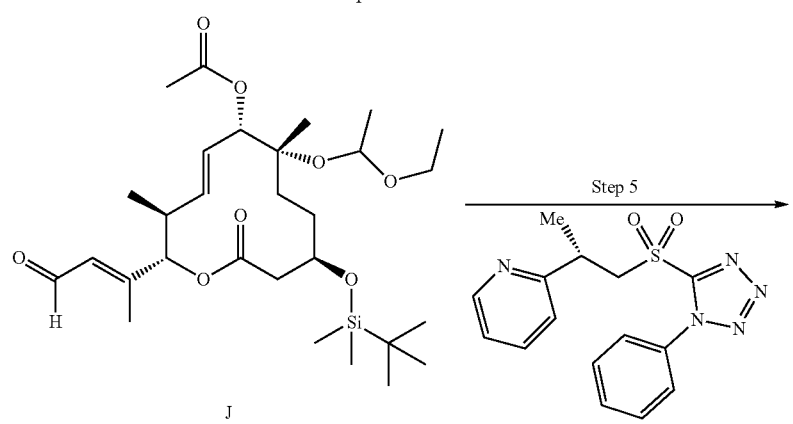
J
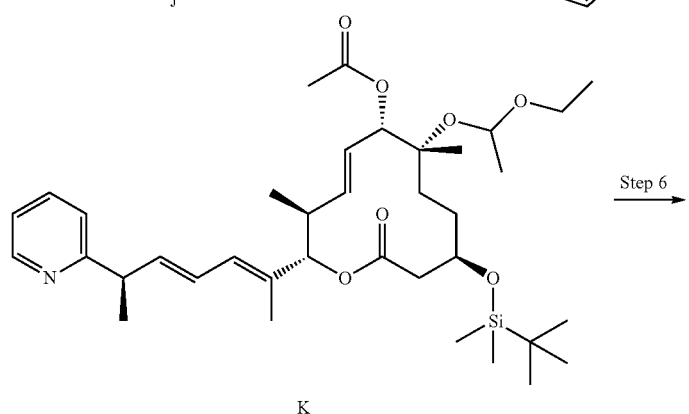
K
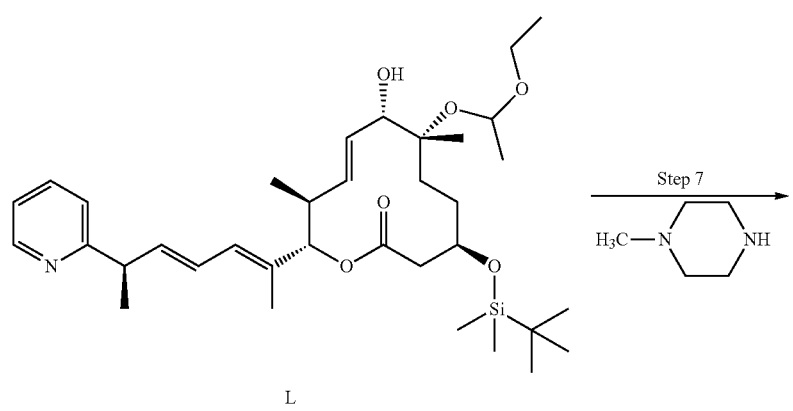
L

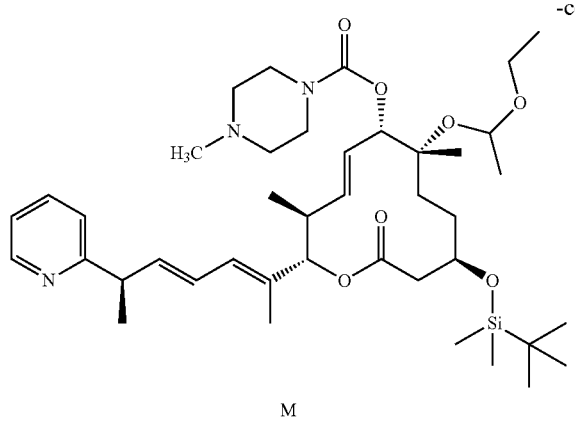

M

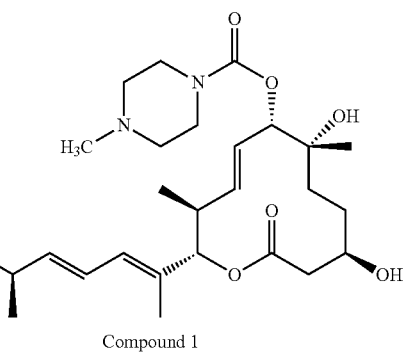

Compound 1

Step 1: Synthesis of (2S,3S,6S,7R,10R,E)-10-((tert-butyldimethylsilyl)oxy)-2-((R,2E,4E)-7-((2R,3R)-3-((2S,3S)-3-((tert-butyldimethylsilyl)oxy)pentan-2-yl)oxiran-2-yl)-6-hydroxy-6-methylhepta-2,4-dien-2-yl)-7-hydroxy-3,7-dimethyl-12-oxooxacyclododec-4-en-6-yl acetate. A solution of pladienolide D (F, 5.3 g, 9.7 mmol, 1.0 equiv.) under nitrogen in DMF (80 mL, 0.1M) at 0° C. was treated with imidazole (4.6 g, 67.8 mmol, 7.0 equiv.) and TBSCl (7.3 g, 48.4 mmol, 5.0 equiv.). The reaction was allowed to warm to room temperature and stirred for 20 hours, or until the reaction was determined to be complete by LCMS or TLC. The reaction was extracted with ethyl acetate and the organic layer was washed with brine, dried over sodium sulfate, filtered, and concentrated in vacuo. The resulting oil was purified by silica gel column chromatography (hexanes/ethyl acetate as eluent) to afford the desired product (G, 7.5 g, 9.6 mmol, 99%).

Step 2: Synthesis of (2S,3S,6S,7R,10R,E)-10-((tert-butyldimethylsilyl)oxy)-2-((6R,E)-7-((2R,3S)-3-((ter/-butyldimethylsilyl)oxy)pentan-2-yl)oxiran-2-yl)-4,5,6-trihydrox-6-methylhept-2-en-2-yl)-7-hydroxy-3,7-dimethyl-12-oxooxacyclododec-4-en-6-yl acetate. To a solution of olefin G (7.6 g, 9.7 mmol, 1.0 equiv.) in degassed TEF:H$_2$O (210 mL:21 mL, 0.01M) under nitrogen at 0° C. was added osmium tetroxide (24.4 mL, 1.9 mmol, 0.2 equiv., 2.5% solution in tert-butanol) followed by N-methylmorpholine N-oxide (2.3 g, 19.5 mmol, 2.0 equiv.). The reaction was allowed to warm to room temperature and stirred for 13 hours, or until the reaction was determined to be complete by LCMS or TLC. The reaction was quenched with sodium sulfite, diluted with ethyl acetate, and the organic layer was washed with water, dried over magnesium sulfate, filtered, and concentrated in vacuo. The resulting oil was purified by silica gel column chromatography (dichloromethane/methanol as eluent) to afford the desired product (H, 6.8 g, 8.3 mmol, 86%).

Step 3: Synthesis of (2S,3S,6S,7R,10R,E)-10-((tert-butyldimethylsilyl)oxy)-7-hydroxy-3,7-dimethyl-12-oxo-2-((E)-4-oxobut-2-en-2-yl)oxacyclododec-4-en-6-yl acetate. To a solution of diol H (7.9 g, 9.7 mmol, 1.0 equiv.) in benzene (350 mL, 0.03M) under nitrogen at room temperature was added lead tetraacetate (8.6 g, 19.4 mmol, 2.0 equiv.). The reaction was stirred for 30 minutes, or until the reaction was determined to be complete by LCMS or TLC. The reaction was concentrated and purified by silica gel column chromatography (hexane/ethyl acetate as eluent) to afford the desired product (I, 2.5 g, 5.26 mmol, 54%).

Step 4: Synthesis of (2S, 3S, 6S, 7R, 10R,E)-10-((tert-butyldimethylsilyl)oxy)-7-(1-ethoxyethoxy)-3,7-dimethyl-12-oxo-2-((E)-4-oxobut-2-en-2-yl)oxacyclododec-4-en-6-yl acetate. To a solution of aldehyde I (1.4 g, 2.9 mmol, 1.0 equiv.) in THF (9.5 mL, 0.5M) was added ethoxyethene (11.1 mL, 40.0 equiv.) and pyridinium p-toluenesulfonate (0.07 g, 0.3 mmol, 0.1 equiv.) at room temperature. The reaction was stirred for 24 hours, or until the reaction was determined to be complete by LCMS or TLC. The reaction was quenched with sodium bicarbonate and diluted with ethyl acetate. The ethyl acetate was washed with water, brine, dried over magnesium sulfate, filtered, and concentrated in vacuo. The resulting oil was purified by silica gel column chromatography (hexane/ethyl acetate as eluent) to afford the desired product (J, 1.2 g, 2.2 mmol, 75%).

Step 5: Synthesis of (2S,3S,6S,7R, 10R,E)-10-((tert-butyldimethylsilyl)oxy)-7-(1-ethoxyethoxy)-3,7-dimethyl-12-oxo-2-((R,2E,4E)-6-(pyridin-2-yl)hepta-2,4-dien-2-yl)oxacyclododec-4-en-6-yl) acetate. To a solution of (S)-2-(1-((1-phenyl-1H-tetrazol-5-yl)sulfonyl)propan-2-yl)pyridine (UUUUU) (695.0 mg, 2.1 mmol, 1.5 equiv.) in THF (20 mL, 0.06M) under nitrogen at −78° C. was added KHMDS (4.2 mL, 2.1 mmol, 1.5 equiv.) dropwise and the reaction was stirred for 20 minutes. Then aldehyde J (780.0 mg, 1.4 mmol, 1.0 equiv.) in THF (1.0 mL) was added dropwise. The reaction was stirred at −78° C. for 90 minutes and then allowed to warm to −20° C. for 1 hour. The reaction was quenched with ammonium chloride, diluted with ethyl acetate, and warmed to room temperature. The organic layer was washed with water, brine, dried over magnesium sulfate, filtered, and concentrated in vacuo. The resulting oil was purified by silica gel column chromatography (hexane/ethyl acetate as eluent) to afford the desired *Julia* product (K, 490 mg, 0.7 mmol, 53%).

Step 6: Synthesis of (4R,7R,8S,11S,E)-4-((tert-butyldimethylsilyl)oxy)-7-(1-ethoxyethoxy)-8-hydroxy-7,11-dimethyl-12-((R,2E,4E)-6-(pyridin-2-yl)hepta-2,4-dien-2-yl)oxacyclododec-9-en-2-one. To a solution of acetate K (490 mg, 0.7 mmol, 1.0 equiv.) in methanol (15 mL, 0.05M) at room temperature was added potassium carbonate (155 mg, 0.4 mmol, 1.5 equiv.). The reaction was run for 24 hours, or until the reaction was determined to be complete by LCMS or TLC. The reaction was quenched with water, diluted with ethyl acetate, washed with brine, dried over magnesium sulfate, filtered, and concentrated in vacuo. The resulting foamy solid (L, 459 mg, 0.7 mmol, 100%) was advanced into the next step without additional purification.

Step 7: Synthesis of (2S,3S,6S,7R,10R,E)-10-((tert-butyldimethylsilyl)oxy)-7-(1-ethoxyethoxy)-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate. To a solution of alcohol L (459 mg, 0.7 mmol, 1.0 equiv.) in dichloromethane (0.5 mL, 0.1M) at room temperature was added N,N-dimethylaminopyridine (27.3 mg, 0.2 mmol, 0.3 equiv.) and triethylamine (1.0 mL, 7.4 mmol, 10.0 equiv.) followed by 4-nitrophenyl chloroformate (451 mg, 02.2 mmol, 3:0 equiv.). The reaction was stirred at room temperature for three hours. Next, N-methyl-piperazine (299 mg, 2.98 mmol, 4.0 equiv.) was added at room temperature. After stirring for one hour, the reaction was quenched with water and diluted with dichloromethane. The organic layer was washed with 1N sodium hydroxide solution, and the organic layer was concentrated. The resulting oil was purified by silica gel column chromatography (hexanes/ethyl acetate as eluant) to afford the desired product (M, 553 mg, 0.75 mmol, 100%).

Step 8: Synthesis of (2S,3S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate (Compound 1). To a solution of silyl ether (M, 553 mg, 0.74 mmol, 1.0 equiv.) in methanol (20 mL, 0.04M) at room temperature was added p-methoxytoluenesulfonic acid (425 mg, 2.2 mmol, 3.0 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired Compound 1 (184 mg, 0.33 mmol, 44%). $^1$H NMR (400 MHz, CHLOROFORM-d) δ: 0.82-1.00 (m, 3H) 1.22-1.48 (m, 8H) 1.50-1.63 (m, 1H) 1.66-1.83 (m, 4H) 1.97 (s, 1H) 2.07 (s, 1H) 2.33 (s, 3H) 2.40 (br. s., 3H) 2.45-2.68 (m, 3H) 3.44-3.61 (m, 5H) 3.74 (dd, J=14.2, 7.2 Hz, 2H) 5.04 (d, J=9.3 Hz, 1H) 5.17 (d, J=10.5 Hz, 1H) 5.57-5.76 (m, 2H) 6.02 (dd, J=15.1, 7.5 Hz, 1H) 6.13 (d, J=10.8 Hz, 1H) 6.34 (ddd, J=15.1, 10.7, 1.0 Hz, 1H) 7.14 (t, J=6.2 Hz, 1H) 7.18 (d, J=7.4 Hz, 1H) 7.63 (t, J=7.3 Hz, 1H) 8.57 (d, J=5.1 Hz, 1H). MS (ES+)=556.4 [M+H].

Exemplary Synthesis of Crystalline Form 1

Free base of compound of Formula I (290 mg, 0.52 mmol, 1 wt, 1 vol) was suspended in MTBE (3.22 g, 11 wt, 4.35 ml, 15 vol) and heated to gentle reflux whereupon white precipitate formed. N-Heptane (2.98 g, 10.3 wt, 4.35 ml, 15 vol) was added while maintaining T-internal ≥52° C. The resultant mixture was heated at gentle reflux for 5 minutes, cooled down to room temperature over 20 minutes, and then further down to −5° C. After stirring at −5° C. for 10 minutes, white precipitate was collected by filtration, rinsed with a mixture of n-heptane (1.50 ml, 5.2 vol) and MTBE (0.50 ml, 1.7 vol), dried under nitrogen/vacuum for 5 minutes, and then transferred to a vial and further dried under vacuum for 1 hour to give Form 1 as a white crystalline powder (206 mg, 0.37 mmol, 0.71 wt, 71% yield).

Exemplary Synthesis of Crystalline Form 1

Free base of compound of Formula I from 2 batches (8.17 g+4.10 g; total 12.27 g, 22.1 mmol, 1 wt, 1 vol) was consolidated into 500 ml flask (3×10 ml THF used for transfer) and concentrated to give 16.41 g of yellow oil, which was suspended/dissolved in MTBE (61.4 ml, 5 vol). Some white precipitate formed shortly after MTBE addition. The mixture was concentrated under vacuum for solvent exchange to give 15.48 g light yellow solid (~3 g solvents remained). MTBE (86 ml, 7 vol) was added (25° C.) and the mixture was heated at 50-53° C. for 0.5 hours to achieve free flowing suspension. n-Heptane (86 ml, 7 vol) was added while maintaining T-internal ≥50° C. (over 10 min). Heating was turned off and the mixture was allowed to cool down to room temperature (0 h: 54° C.; 0.5 h: 38° C.; 1 h: 28° C.; 2.5 h: 25° C.). After 2.5 hours, the precipitate was collected by filtration, rinsed with a mixture of MTBE (10 ml, 0.82 vol) and N-heptane (20 ml, 1.6 vol) and dried under nitrogen/vacuum for 2 hours to give Form 1 as off-white crystalline powder (9.05 g, 16.3 mmol, 0.74 wt, 73.8% yield).

Exemplary Synthesis of Crystalline Form 1

Free base of compound of Formula I (with residual solvents; 379 mg, 0.682 mmol, 1 wt, 1 vol, 1 eq) was dissolved in MTBE (2.75 ml, 7 vol) and heated to 50° C. (white precipitate formed at around 40° C.). N-Heptane (2.75 ml, 7 vol) was added while maintaining T-internal above 50° C. Upon complete addition, the mixture was allowed to cool down. After 1 hour (25° C.), precipitate was collected by filtration (sonication applied to loosen the solid), rinsed with a mixture of MTBE (0.79 ml, 2 vol) and N-heptane (0.79 ml, 2 vol) and dried under nitrogen/vacuum at ambient temp for 1 hour to give Form 1 as white crystalline powder (205 mg, 0.37 mmol, 0.54 wt, 54% yield).

Exemplary Synthesis of Crystalline Form 1

Free base of compound of Formula I (0.380 g, 0.684 mmol, 1 wt, 1 vol, 1 eq) was dissolved in ethyl acetate (1.14 ml, 3 vol) and heated to 65° C. (white precipitate formed at around 40° C.). N-heptane (3.42 ml, 9 vol) was added while controlling T-internal above 65° C. The resultant suspension was allowed to cool down to room temperature with stirred overnight. Precipitate was collected by filtration (sonication applied to loosen the solid), rinsed with a mixture of n-heptane (0.95 ml, 2.5 vol) and ethyl acetate (0.19 ml, 0.5 vol) and dried under nitrogen/vacuum for 1 hour to give Form 1 as white crystalline powder (230 mg, 0.414 mmol, 0.605 wt, 60.5% yield).

X-Ray Powder Diffraction

XRPD diffractograms of the crystalline Form 1 were obtained using a X'Pert Pro diffractometer (Yamato Scientific Co., Ltd.) in the transmission mode. Sample was placed between two Mylar films and fixed with sample holder. Analytical conditions for the XRPD diffractograms are shown in Table 2 below.

TABLE 2

Analytical conditions for XRPD diffractograms

| | |
|---|---|
| X-ray source | CuKα |
| Detector | Semiconductor array detector |
| Tube voltage | 45 kV |
| Tube ampere | 40 mA |
| Soller slit | 0.02 radian |
| Scan speed | 0.042 deg/min |
| Step size | 0.017 deg |
| Scan range | 3 to 40 deg |

TABLE 3

Exemplary peak listing for crystalline Form 1

| Degrees 2 Theta (° 2θ) | d (Å) |
|---|---|
| 5.869 | 15.05997 |
| 7.749 | 11.40903 |
| 12.837 | 6.89629 |
| 15.105 | 5.86545 |
| 15.276 | 5.80015 |
| 15.569 | 5.69171 |
| 15.940 | 5.56006 |
| 16.102 | 5.50441 |
| 18.220 | 4.86914 |
| 19.295 | 4.60026 |
| 19.947 | 4.45144 |
| 20.325 | 4.36934 |
| 21.184 | 4.19416 |
| 21.356 | 4.16077 |
| 23.586 | 3.77217 |
| 25.817 | 3.45100 |

FIG. 1 contains an exemplary XRPD diffractogram of crystalline Form 1.

Single Crystal X-Ray Diffraction

Single crystal X-ray diffraction analysis was used to solve the crystal structure of crystalline Form 1. The free base compound of Formula I (12.21 mg) was dissolved in ethyl acetate (1 mL) and n-heptane (1 mL) was added. Crystals were grown by slow evaporation method at room temperature for 1 day. A colorless single crystal (0.3×0.2×0.1 mm) was mounted on a glass fiber. Diffraction data was collected at room temperature on R-AXIS RAPID II-R imaging plate detector system (Rigaku) with ω axis oscillation method using graphite monochromated Cu-Kα radiation.

Figure 6:
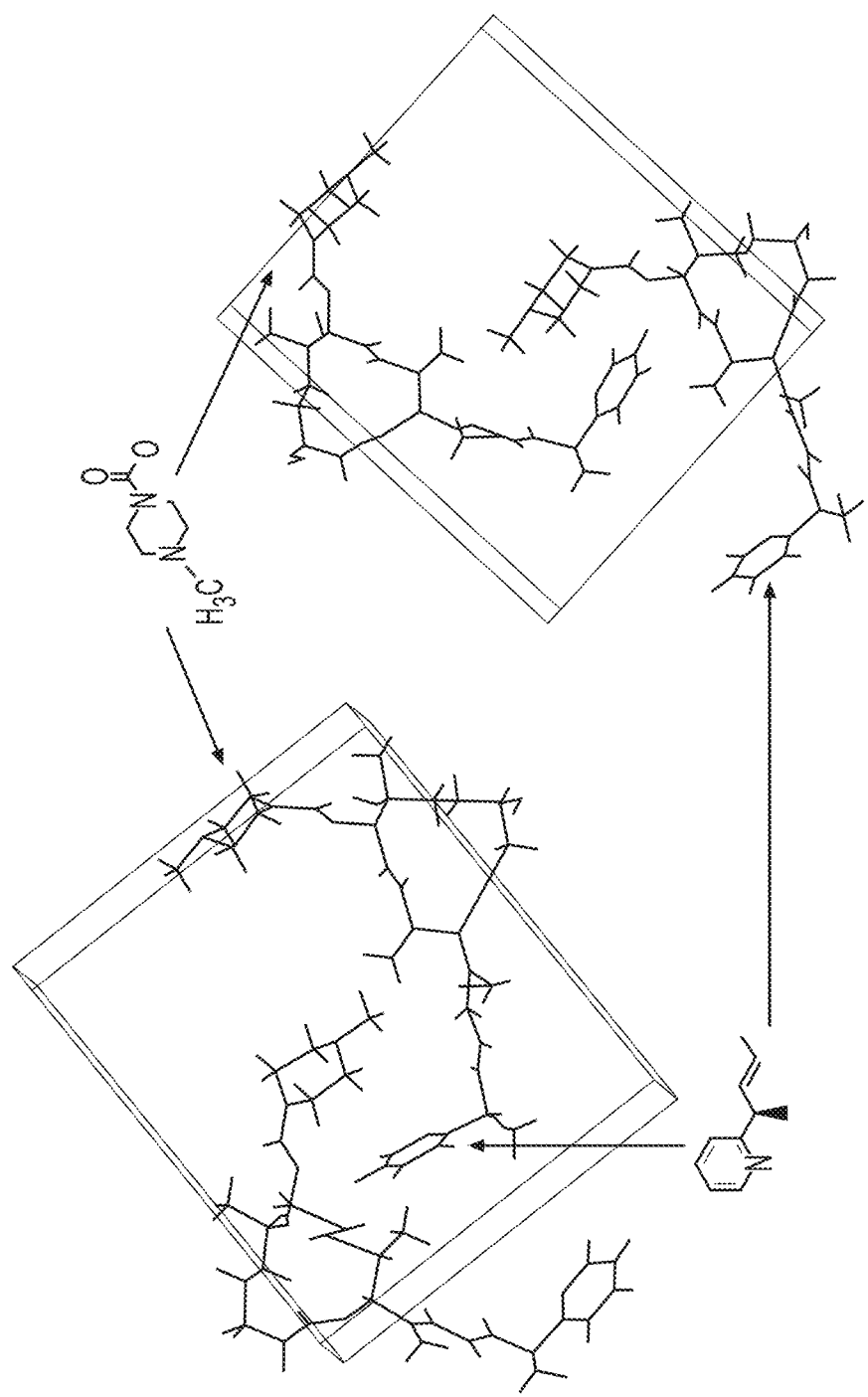
FIG. 6 is a depiction of the proposed crystal packing in crystalline Form 1.

Crystal data and structure refinement data for Form 1 are summarized in Table 4. The solved structure is believed to comprise two molecules of the free base compound of Formula I oriented nearly opposite from each other in each unit cell. FIG. 6 is a depiction of the proposed crystal packing of Form 1.

TABLE 4

Crystal Data and Structure Refinement for Form I

| Parameter | Value |
|---|---|
| Empirical formula | C31 H45 N3 O6 |
| FW | 555.70 |
| Space group | P 2$_1$ |
| Unit cell dimensions: | |
| a [Å] | 5.9306(2) |
| b [Å] | 17.4303(6) |
| c [Å] | 15.1800(5) |
| α [°] | 90° |
| β [°] | 99.641(2) |
| γ [°] | 90° |
| V [Å$^3$] | 1547.03(9) |
| Z | 2 |
| D$_c$ [Mg/cm$^3$] | 1.220 |
| Crystal size [mm$^3$] | 0.3 × 0.2 × 0.1 |
| Temperature (K) | 173(2) |
| Radiation (wavelength, Å) | 1.54178 |
| Monochromator | Fixed monochromator |
| Linear abs coef, mm−1 | 0.682 |
| Data collection | |
| No. of Reflections Measured | Total: 15656 |
|  | Unique: 5363 |
| Completeness | 0.981 |
| R$_{merge}$ [1)] | 0.05849 |
| Structure Solution and Refinement | |
| Structure Solution | Direct Methods (SHELXS97) |
| Refinement | Full-matrix least-squares on F$^2$ |
| No. of Reflections | 5363 |
| No. of Variables | 361 |
| Residuals: R; Rw [2)] | 0.1118; 0.1983 |

Figure 7:
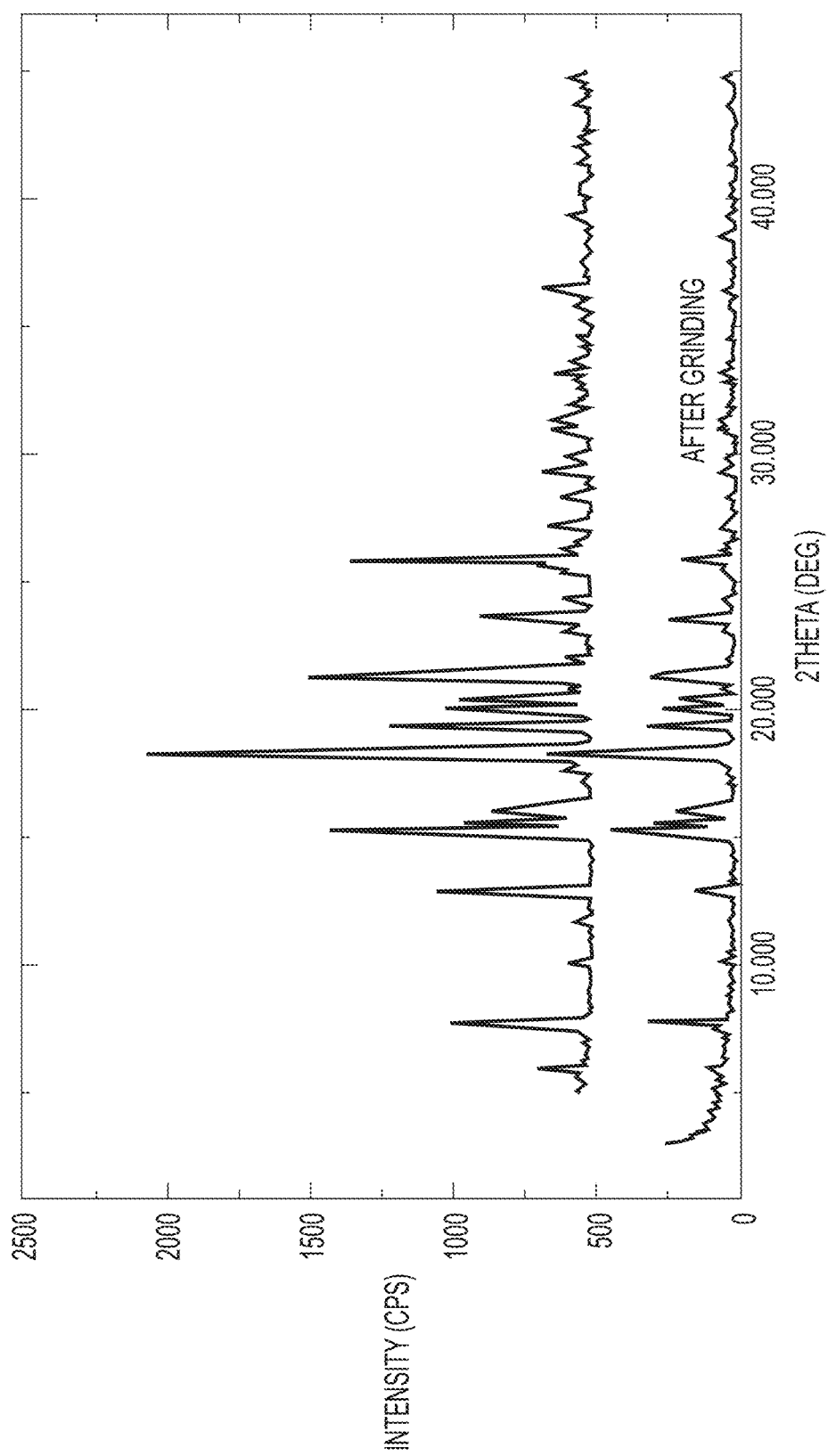
FIG. 7 shows XRPD diffractograms of a sample of crystalline Form 1 before and after grinding.

Grinding a sample of crystalline Form 1 with a mortar and pestle resulted in a change in the X-ray diffractogram as shown in FIG. 7, possibly indicating the formation of amorphous material.

Solid state stability studies were carried out on crystalline Form 1 under the following conditions:
Stored at 25° C. for 7 and 14 days
Stored at 40° C./75% RH (open) for 7 and 14 days
Stored at 60° C. for 7 and 14 days No significant degradation was observed under those conditions, and XRPD and TGA-DSC analyses of the sample stored at 40° C./75% RH (open) for 14 days showed no change in crystallinity.

Biological Assays

Cell Viability Assay Protocol

Cells (WiDr and Panc05.04 obtained from ATCC) were seeded in 96-well plates, with 2000 cells/100μ4/well, and incubated overnight. Spent media was removed, and fresh, media containing 9 different concentrations of compound (100μ4/well) were added, with DMSO concentration from compound stock solution adjusted to be 0.1%. Each compound treatment was done in duplicate or triplicate at each concentration.

Another plate with cells seeded was dedicated as a time zero (Tz) plate, to which was added 0.1% DMSO in media (100μ4/well) followed by CellTiter-Glo® reagent (Promega Corporation, Madison, Wis.) (50μ4/well) for ATP measurement as a surrogate of cell viability. Average value from measurement of multiple wells of this plate is used as Tz.

Compound-treated plates were incubated for 72 hr at 37° C. Then, CellTiter-Glo® reagent (50μ4/well) was added and ATP was measured. Average value from measurement of the duplicate or triplicate compound-treated wells is used as Ti, and seeded plates with medium having 0.1% DMSO without compound is used as control growth (C).

Percentage growth inhibition/Percentage viability was calculated as:

$[(Ti-Tz)/(C-Tz)] \times 100$ for concentrations for which $Ti \geq Tz$ $[(Ti-Tz)/Tz] \times 100$ for concentrations for which $Ti < Tz$.

*time zero (Tz), control growth (C), and test growth in the presence of compound (Ti) Percentage growth inhibition/Percentage viability are plotted versus compound concentration to determine E$_{max}$.

Growth inhibition of 50% (GI$_{50}$) was calculated from $[(Ti-Tz)/(C-Tz)] \times 100 = 50$, which is the drug concentration resulting in a 50% reduction in the net increase of ATP in control growth (C) during the compound treatment.

In Vitro Splicing (Biochemical) Assay Protocol

Biotin-labeled pre-mRNA of an adenovirus type 2 construct with a deletion of intervening sequence (Ad2) (Berg, M. G., et al. 2012 Mol. Cell Bio., 32(7):1271-83) was prepared by in vitro transcription. The Ad2 construct containing Exon 1 (41 nucleotides), Intron (231 nucleotides), and Exon 2 (72 nucleotides) was generated by gene synthesis and cloned into the EcoRI and XbaI sites of pGEM®-3Z vector (Promega) by Genewiz® (South Plainfield, N.J.). The plasmid was then linearized by XbaI digestion and purified. In vitro transcription and purification of transcribed pre-mRNA were performed using the MEGAscript® T7 transcription kit (Invitrogen™, Life Technologies™, Grand Island, N.Y.) and MEGAclear™ transcription clean-up kit (Invitrogen™, Life Technologies™, Grand Island, N.Y.), respectively, following the manufacturer's instructions. The ratio of biotin-16-UTP (Roche Diagnostics Corporation, Indianapolis, Ind.) to cold UTP was 1:13 to incorporate approximately two biotin molecules per spliced Ad2 mRNA.

In vitro splicing assay was performed at 30° C. in 254 reaction mixtures containing 95 µg HeLa nuclear extract (Promega Corporation, Madison, Wis.), 47 nM Ad2 pre-mRNA, 25U RNasin RNase inhibitor (Promega Corporation, Madison, Wis.), 1×SP buffer (0.5 mM ATP, 20 mM creatine phosphate, 1.6 mM $MgCl_2$), and compounds in DMSO (with 1% final concentration of DMSO). After 90 min of incubation, the reaction was stopped by addition of 184 of 5M NaCl, and the mixtures were incubated with 10 µL of M-280 streptavidin-coated magnetic beads (Invitrogen™ Life Technologies™, Grand Island, N.Y.) for 30 min at room temperature to capture Ad2 pre- and spliced mRNA. The beads were washed twice with 1004 buffer containing 10 mM Tris pH=7.5, 1 mM EDTA and 2M NaCl, and then incubated in RNA gel loading buffer containing 95% formamide at 70° C. for 10 min to elute the RNAs. Ad2 RNAs were resolved by 6% TBE-UREA gel, transferred to a nylon membrane, UV cross-linked, and probed with an IRDye® labeled streptavidin (LI-COR, Lincoln, Nebr.). The amount of spliced RNA was quantified by measuring the band fluorescent intensity using LI-COR Image Studio software.

Results

Data are reported in Table 5 below. $E_{max}$ refers to the maximum achievable response to a compound in a tested dose range, with a negative value indicating cellular lethality. A larger negative $E_{max}$ value indicates greater cellular lethality for a particular compound.

WIDr-R cells are colon cancer cells which have a chemically-induced R1074H mutation and have been shown to be resistant to pladienolide B in terms of growth inhibition (Yokoi, A., et al., 2011 FEBS Journal, 278:4870-4880). The counter-screening of compounds in this viability assay with a "resistant" WiDr-R cell line may indicate whether these compounds have off-target effect(s). Compounds that lack growth inhibitory ($GI_{50}$) activity in the resistant WiDr-R cell line but maintain activity in the parental WiDr cell line suggests that on-mechanism splicing modulation is responsible for the growth inhibition which is observed in the parental WiDr cell line.

The in vitro splicing (IVS) assay described above is a biochemical assay that monitors inhibition of the splicing of an exemplary pre-mRNA into an mRNA. This biochemical assay enables researchers to assess at what compound concentration splicing of this particular transcript is inhibited in a non-cellular context and is used to demonstrate mechanistic splicing inhibitory activity.

TABLE 5

Biological Activity of Compound 1

| Compound number | Panc 05.04 (mt SF3B1 cells) $E_{max}$ (%) | Panc 05.04 (mt SF3B1 cells), $GI_{50}$ (nM) | WiDr GI50 (nM) | WiDr-R $GI_{50}$ (nM) | In vitro splicing (IVS) assay (nM) |
|---|---|---|---|---|---|
| 1 | −66.09 | 32.72 | 31.78 | >1000 | 1330.00 |

Key
Panc 05.04 cells: Pancreatic cancer cells, mutant SF3B1 cell line (Q699H and K700E mutations in SF3B1)
WiDr cells: Colon cancer cells (wildtype SF3B1)
WiDr-R cells: Colon cancer cells (chemically-induced SF3B1 mutant which is resistant to E7107 (R1074H mutation))

We claim:

1. Crystalline Form 1 of (2S,3S,6S,7R,10R,E)-7,10-dihydroxy-3,7-dimethyl-12-oxo-24(R,2E,4E)-6-(pyridin-2-yehepta-2,4-dien-2-yeoxacyclododec-4-en-6-yl 4-methylpiperazine-1-carboxylate having an X-ray powder diffractogram which has at least one peak chosen from peaks (° 2θ) at 5.9°±0.2°, 7.7°±0.2°, 12.8°±0.2°, 15.3°±0.2°, 18.2°±0.2°, 19.3°±0.2°, 21.2°±0.2°, 23.6°±0.2°, and 25.8°±0.2°.

2. The crystalline Form 1 according to claim 1, wherein the X-ray powder diffractogram has a peak (°2θ) at 5.9°±0.2°.

3. The crystalline Form 1 according to claim 1, wherein the X-ray powder diffractogram has a peak (° 2θ) at 7.7°±0.2°.

4. The crystalline Form 1 according to claim 1, wherein the X-ray powder diffractogram has a peak (° 2θ) at 12.8°±0.2°.

5. The crystalline Form 1 according to claim 1, wherein the X-ray powder diffractogram has a peak (° 2θ) at 15.3°±0.2°.

6. The crystalline Form 1 according to claim 1, wherein the X-ray powder diffractogram has a peak (° 2θ) at 18.2°±0.2°.

7. The crystalline Form 1 according to claim 1, wherein the X-ray powder diffractogram has a peak (° 2θ) at 19.3°±0.2°.

8. The crystalline Form 1 according to claim 1, wherein the X-ray powder diffractogram has a peak (° 2θ) at 21.2°±0.2°.

9. The crystalline Form 1 according to claim 1, wherein the X-ray powder diffractogram has a peak (° 2θ) at 23.6°±0.2°.

10. The crystalline Form 1 according to claim 1, wherein the X-ray powder diffractogram has a peak (° 2θ) at 25.8°±0.2°.

11. The crystalline Form 1 according to claim 1, wherein the X-ray powder diffractogram has peaks (° 2θ) at 7.7°±0.2°, 15.3°±0.2°, and 18.2°±0.2°.

12. The crystalline Form 1 according to claim 1, wherein the X-ray powder diffractogram has peaks (° 2θ) at 7.7°±0.2°, 15.3°±0.2°, 18.2°±0.2°, 19.3°±0.2°, and 21.2°±0.2°.

13. The crystalline Form 1 according to claim 1, wherein the X-ray powder diffractogram has at least two peaks chosen from peaks (° 2θ) at 5.9°±0.2°, 7.7°±0.2°, 12.8°±0.2°, 15.3°±0.2°, 18.2°±0.2°, 19.3°±0.2°, 21.2°±0.2°, 23.6°±0.2°, and 25.8°±0.2°.

14. The crystalline Form 1 according to claim 1, wherein the crystalline Form 1 has an X-ray powder diffractogram substantially as shown in FIG. 1.

15. A pharmaceutical composition comprising a therapeutically effective amount of the crystalline Form 1 according to claim 1 and at least one additional component chosen from a pharmaceutically acceptable carrier, a pharmaceutically acceptable vehicle, and a pharmaceutically acceptable excipient.

16. A pharmaceutical composition consisting essentially of a therapeutically effective amount of the crystalline Form 1 according to claim 1 and at least one additional component chosen from a pharmaceutically acceptable carrier, a pharmaceutically acceptable vehicle, and a pharmaceutically acceptable excipient.

17. A pharmaceutical composition consisting of a therapeutically effective amount of the crystalline Form 1 according to claim 1 and at least one additional component chosen from a pharmaceutically acceptable carrier, a pharmaceutically acceptable vehicle, and a pharmaceutically acceptable excipient.

18. A method for treating cancer in a subject, comprising administering to a subject in need thereof a therapeutically effective amount of the crystalline Form 1 according to claim 1, wherein the cancer is chosen from acute lymphoblastic leukemia, acute myeloid leukemia, breast cancer, cholangiocarcinoma, chronic lymphocytic leukemia, chronic myelomonocytic leukemia, colon cancer, endometrial cancer, gastric cancer, lung cancer, myelodysplastic syndrome, ovarian cancer, pancreatic cancer, and uveal melanoma.

19. The method according to claim 18, wherein the cancer is chosen from acute lymphoblastic leukemia, acute myeloid leukemia, chronic lymphocytic leukemia, and chronic myelomonocytic leukemia.

20. The method according to claim 18, wherein the cancer is colon cancer.

21. The method according to claim 18, wherein the cancer is pancreatic cancer.

22. The method according to claim 18, wherein the cancer is positive for one or more mutations in a spliceosome gene or protein.

23. The method according to claim 22, wherein the spliceosome gene or protein is splicing factor 3B subunit 1.

24. A method for treating cancer in a subject, comprising administering to a subject in need thereof a therapeutically effective amount of the pharmaceutical composition according to claim 7, wherein the cancer is chosen from acute lymphoblastic leukemia, acute myeloid leukemia, breast cancer, cholangiocarcinoma, chronic lymphocytic leukemia, chronic myelomonocytic leukemia, colon cancer, endometrial cancer, gastric cancer, lung cancer, myelodysplastic syndrome, ovarian cancer, pancreatic cancer, and uveal melanoma.

25. The method according to claim 24, wherein the cancer is positive for one or more mutations in a spliceosome gene or protein.

26. The method according to claim 25, wherein the spliceosome gene or protein is splicing factor 3B subunit 1.

* * * * *

UNITED STATES PATENT AND TRADEMARK OFFICE
CERTIFICATE OF CORRECTION

PATENT NO. : 10,745,387 B2
APPLICATION NO. : 15/529798
DATED : August 18, 2020
INVENTOR(S) : Gregg F. Keaney et al.

It is certified that error appears in the above-identified patent and that said Letters Patent is hereby corrected as shown below:

In the Claims

Claim 1, Column 28, Lines 20-23, "(2S,3S,6S,7R,10R,E)-7,10-dihydroxy-3,7-dimethyl-12-oxo-24(R,2E,4E)-6-(pyridin-2-yehepta-2,4-dien-2-yeoxacyclododec-4-en-6-yl 4-methylpiperazine-1-carboxylate" should read as --"(2S,3S,6S,7R,10R,E)-7,10-dihydroxy-3,7-dimethyl-12-oxo-24(R,2E,4E)-6-(pyridin-2-yl)hepta-2,4-dien-2-yl)oxacyclododec-4-en-6-yl 4-methylpiperazine-1-carboxylate"--.

Signed and Sealed this
Twenty-eighth Day of March, 2023

Katherine Kelly Vidal
*Director of the United States Patent and Trademark Office*